(12) United States Patent
Dejima et al.

(10) Patent No.: US 8,834,353 B2
(45) Date of Patent: Sep. 16, 2014

(54) MEDICAL MANIPULATOR, TREATMENT SYSTEM, AND TREATMENT METHOD

(75) Inventors: Takumi Dejima, Tokyo (JP); Ken Yamatani, Tokyo (JP); Ayano Ishioka, Tokyo (JP); Kosuke Motai, Tokyo (JP); Kazushi Murakami, Tokyo (JP); Takayasu Mikkaichi, Tokyo (JP)

(73) Assignee: Olympus Medical Systems Corp. (JP)

( * ) Notice: Subject to any disclaimer, the term of this patent is extended or adjusted under 35 U.S.C. 154(b) by 1152 days.

(21) Appl. No.: 12/500,950

(22) Filed: Jul. 10, 2009

(65) Prior Publication Data
US 2010/0056863 A1 Mar. 4, 2010

Related U.S. Application Data

(60) Provisional application No. 61/093,494, filed on Sep. 2, 2008.

(51) Int. Cl.
*A61B 1/00* (2006.01)
*A61B 17/29* (2006.01)
*A61B 1/313* (2006.01)
*A61B 1/04* (2006.01)
*A61B 17/34* (2006.01)
*A61B 19/00* (2006.01)
*A61B 17/00* (2006.01)

(52) U.S. Cl.
CPC ......... *A61B 17/29* (2013.01); *A61B 2017/2906* (2013.01); *A61B 2017/3447* (2013.01); *A61B 2017/2927* (2013.01); *A61B 2019/304* (2013.01); *A61B 1/3132* (2013.01); *A61B 2017/291* (2013.01); *A61B 2017/00323* (2013.01); *A61B 1/04* (2013.01)
USPC .......................................... 600/106; 600/142

(58) Field of Classification Search
CPC ........... A61B 1/00098; A61B 1/00133; A61B 1/00149; A61B 1/00154; A61B 1/0083; A61B 1/0055; A61B 1/0057; A61B 1/008
USPC ................ 600/106, 138–139, 141, 142, 144, 600/148–150
See application file for complete search history.

(56) References Cited

U.S. PATENT DOCUMENTS 4,748,969 A * 6/1988 Wardle .......................... 600/150
4,857,057 A * 8/1989 Sanagi ...................... 604/170.01
(Continued)

FOREIGN PATENT DOCUMENTS

JP        2002-306494     10/2002
JP        A-2005-296412   10/2005
(Continued)

OTHER PUBLICATIONS

Search Report issued by European Patent Office and received by applicant on Sep. 4, 2012 in connection with corresponding EP patent application No. EP 09 011 267.3.

(Continued)

*Primary Examiner* — Alireza Nia
(74) *Attorney, Agent, or Firm* — Ostrolenk Faber LLP

(57) ABSTRACT

A medical manipulator which includes: a plurality of arms formed in a cylindrical shape a distal end portion of which is made of a rigid member having a bending portion capable of bending; an insertion portion made of a rigid member having a plurality of channels in which base ends of the plurality of arms are connected to a distal end of the insertion portion so as to connect lumens of the arms to the plurality of channels; a photographic device provided at the distal end of the insertion portion; an operation portion that operates the bending portion; and a transmission member that connects the bending portion and the operation portion, in which the bending portion has: a first bending portion that is capable of bending in a predetermined direction by an operation of the operation portion, and a second bending portion provided in a base end than the first bending portion that is capable of fixing the plurality of arms in a bent state so as to mutually separate, and the transmission portion has: a first region which is flexible, and a second region which is rigid and connected to a base end portion of the first region.

7 Claims, 34 Drawing Sheets

(56) References Cited

U.S. PATENT DOCUMENTS

| | | | |
|---|---|---|---|
| 5,395,367 A * | 3/1995 | Wilk ................................ 606/1 |
| 7,833,156 B2 * | 11/2010 | Williams et al. .............. 600/184 |
| 2002/0055758 A1 | 5/2002 | Sasaki |
| 2005/0075664 A1 | 4/2005 | Nagase et al. |
| 2005/0096694 A1 | 5/2005 | Lee |
| 2007/0167679 A1 * | 7/2007 | Miyamoto et al. ............ 600/106 |
| 2007/0219550 A1 | 9/2007 | Thompson et al. |
| 2007/0249897 A1 | 10/2007 | Miyamoto et al. |
| 2008/0051631 A1 | 2/2008 | Dejima et al. |

FOREIGN PATENT DOCUMENTS

| | | |
|---|---|---|
| WO | WO 2007/080974 | 7/2007 |
| WO | WO 2007/136683 | 11/2007 |

OTHER PUBLICATIONS

Office Action mailed by Japanese Patent Office on May 14, 2013 in connection with corresponding JP Patent Application No. JP 2009-198302 with English translation.

* cited by examiner

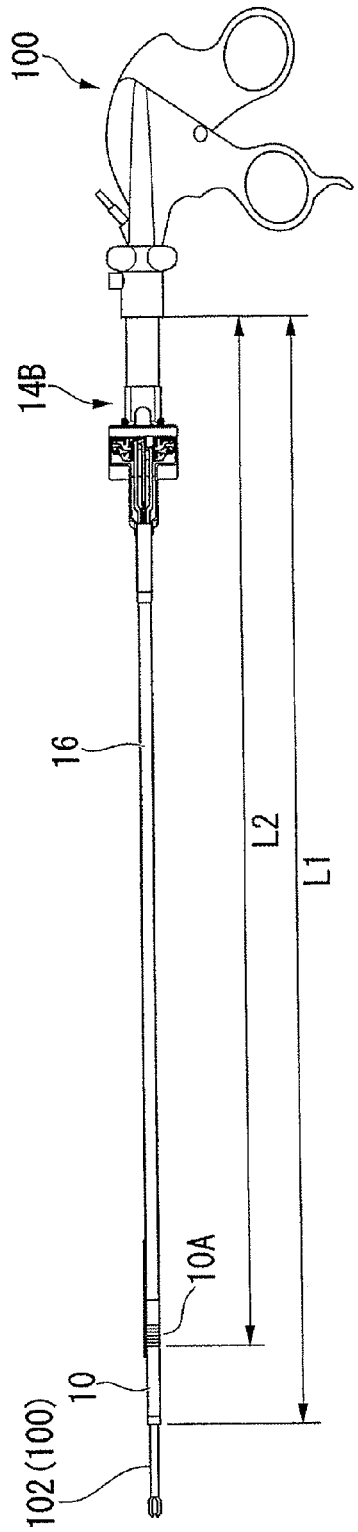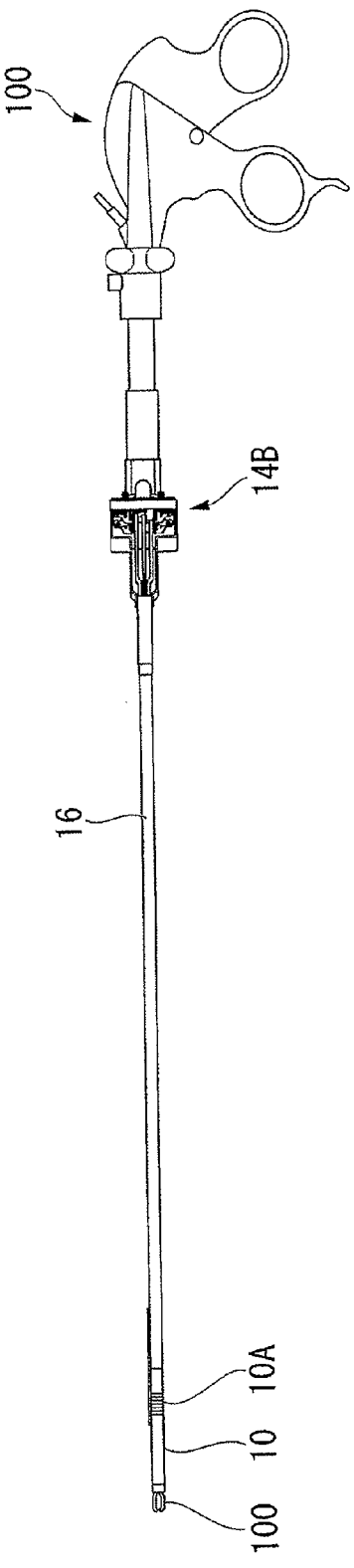
FIG. 14A
FIG. 14B

MEDICAL MANIPULATOR, TREATMENT SYSTEM, AND TREATMENT METHOD

BACKGROUND OF THE INVENTION

1. Field of the Invention

The present invention relates to a medical manipulator, a treatment system which includes the medical manipulator, and a treatment method using the medical manipulator that is inserted into a body cavity and used when performing a procedure on various tissues in a body cavity.

Priority is claimed on U.S. patent application No. 61/093,494, filed Sep. 2, 2008, and U.S. patent application Ser. No. 12/500,950, filed Jul. 10, 2009, the content of which is incorporated herein by reference.

2. Description of Related Art

Conventionally, as an example of low invasive treatment, various procedures such as gallbladder extraction using a laparoscope or the like are performed. This kind of laparoscope procedure is performed by making a plurality of openings in the abdominal wall and a plurality of instruments being inserted therein.

In recent years, in order to reduce the burden on the patent by further reducing the number of openings to be made in the abdominal wall, it has been proposed to perform procedures by inserting a flexible endoscope from the patient's natural orifice such as the mouth, nose, or anus. As a medical device that is used in such a procedure, for example a treatment endoscope has been proposed as disclosed in U.S. Patent Application Publication No. 2007/0249897.

This treatment endoscope has a flexible insertion portion that has flexibility, and a pair of arm portions that have a bending portion that performs a bending action are provided at a distal end of the insertion portion, and a plurality of channels that are disposed in the insertion portion and lumens of the arm portions are continuous. The operating portion of the treatment endoscope is connected to the arm portions by an operating member, and is constituted to be capable of bendably operating the arm portions up/down or left/right.

The user inserts a treatment instrument such as forceps into the channel, mounts an operating portion of the treatment instrument to an operating portion of the treatment endoscope to project the distal end of the treatment instrument from the arm portion and operate the operating portion up/down or left/right, whereby a procedure is performed by causing the distal end of the treatment instrument to approach the tissue of the procedure target from a different direction.

SUMMARY OF THE INVENTION

A first aspect of the present invention is a medical manipulator which includes: a plurality of arms formed in a cylindrical shape a distal end portion of which is made of a rigid member having a bending portion capable of bending, an insertion portion made of a rigid member having a plurality of channels in which base ends of the plurality of arms are connected to a distal end of the insertion portion so as to connect lumens of the arms to the plurality of channels, a photographic device provided at the distal end of the insertion portion, an operation portion that operates the bending portion, and a transmission member that connects the bending portion and the operation portion, in which the bending portion has a first bending portion that is capable of bending in a predetermined direction by an operation of the operation portion and a second bending portion provided in a base end than the first bending portion that is capable of fixing the plurality of arms in a bent state so as to mutually separate, and the transmission portion has a first region which is flexible and a second region which is rigid and connected proximal to the first region.

A second aspect of the present invention is a treatment system which includes: a medical manipulator according to the first aspect and a treatment instrument which is capable of inserting to the channel and the arms of the medical manipulator, in which the treatment instrument has a rigid portion that is provided at the distal end of the treatment instrument and a flexible portion that is connected to a proximal end of the rigid portion, when the treatment instrument is inserted to the medical manipulator to the limit, only the rigid portion is projected from the distal end of the arms and only the flexible portion is located in a lumen of the bending portion.

A third aspect of the present invention is a treatment method using a medical manipulator which has: a plurality of arms formed in a cylindrical shape, a distal end portion of which is made of a rigid member having a bending portion capable of bending, an insertion portion made of a rigid member having a plurality of channels in which base ends of the plurality of arms are connected to a distal end of the insertion portion so as to connect lumens of the arms to the plurality of channels, and a photographic device provided at the distal end of the insertion portion, which includes forming a hole on a body wall that connects to a body cavity, and inserting the number of treatment instruments more than the number of the holes to the body cavity by inserting the treatment instruments to the arms of the medical manipulator.

BRIEF DESCRIPTION OF THE DRAWINGS

FIG. 14A and FIG. 14B are drawings that show the length relation between the manipulator and the inserted treatment instrument.

DETAILED DESCRIPTION OF THE INVENTION

Hereinbelow, a medical manipulator in accordance with a first embodiment of the present invention (hereinbelow simply referred to as the "manipulator") shall be described with reference to FIG. 1 to FIG. 17B.

Figure 1:
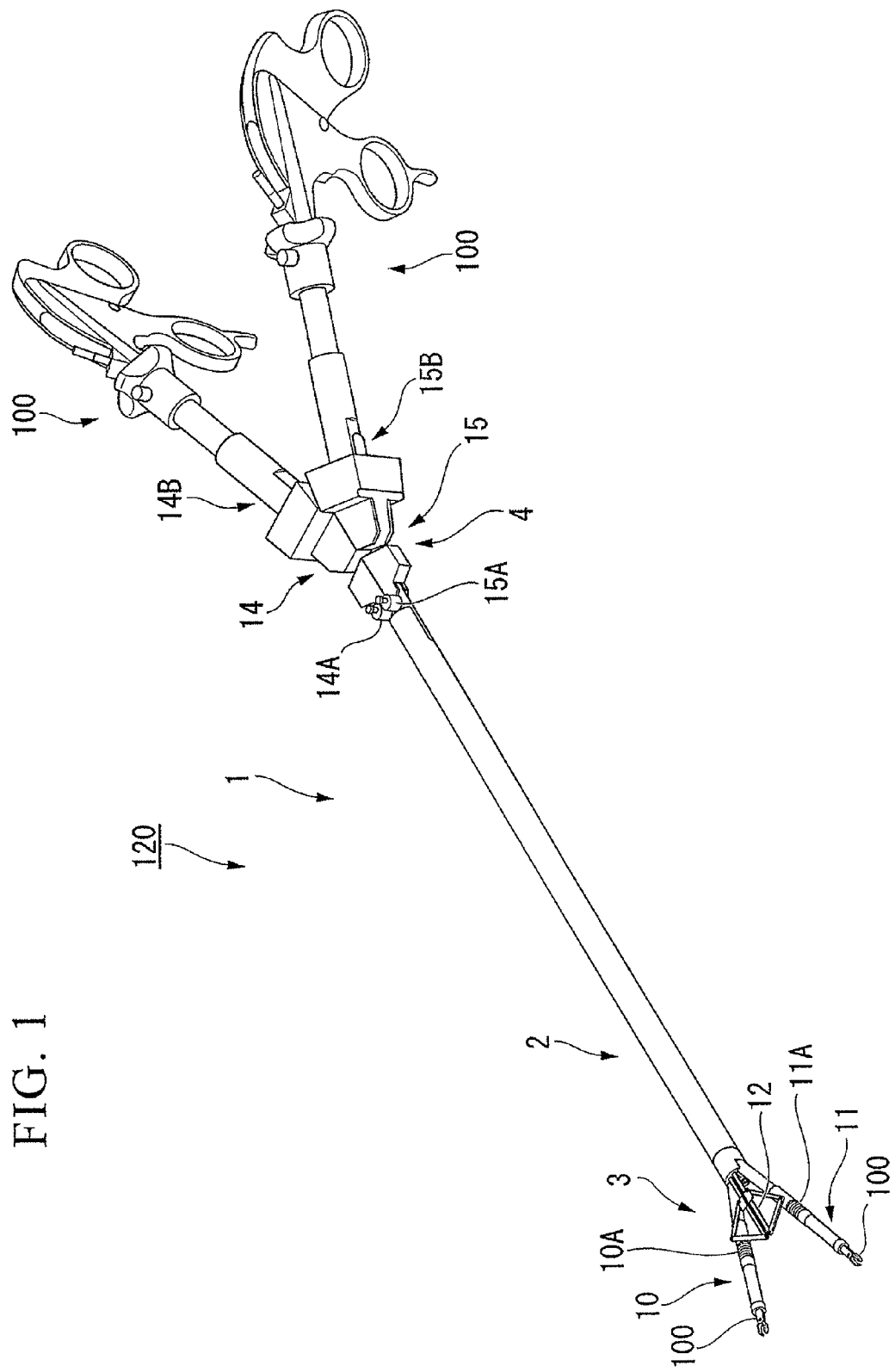
FIG. 1 is an overall view that shows a treatment system which includes a medical manipulator in accordance with a first embodiment of the present invention.

FIG. 1 is an overall view that shows a treatment system 120 which includes a manipulator 1 in accordance with the present embodiment. The treatment system 120 is constituted such that two treatment instruments 100 are inserted to the manipulator 1 of the present embodiment. The manipulator 1 is one that is used by being inserted in a body cavity through a trocar or the like that penetrates the abdominal wall or the like of the patient or a natural orifice such as the mouth, nose, or anus. The manipulator 1 is constituted by being provided with an insertion portion 2 that is inserted in a body cavity, a distal end portion 3 that is attached to the distal end of the insertion portion 2, and an operating portion 4 that is attached to the base end portion of the insertion portion 2.

Figure 2:
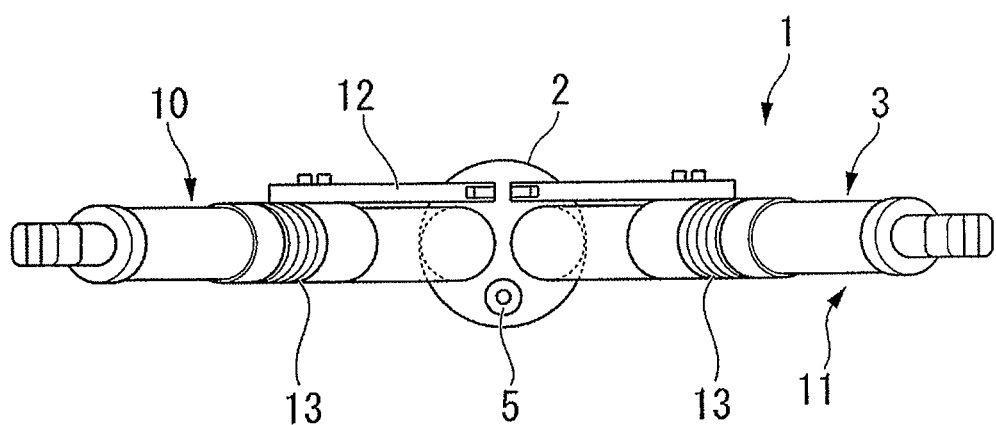
FIG. 2 is a drawing that shows a distal end portion of the insertion portion of a medical manipulator.

The insertion portion 2 is a rigid, tubular member that does not have flexibility, and has two lumens (channels) therein. At the distal end of the insertion portion 2, as shown in FIG. 2, a photographic device 5 is attached. The image signal that the photographic device 5 has obtained is sent to a device such as an image processing device or monitor not illustrated via the insertion portion 2. Thereby, the user is capable of observing ahead of the insertion portion 2 and the distal end portion 3.

The distal end portion 3 is one for performing various procedures on tissue in a body cavity, and is provided with two arms 10 and 11, and a link portion 12 that separates the distal end portion of the arm 10 and the distal end portion of the arm 11 in order to put them in a positional relationship that facilitates the procedure.

The arms 10 and 11 are formed in a tubular shape with a rigid material. The lumens of the arms 10 and 11 are respectively continuous with the channels of the insertion portion 2, and a treatment instrument 100 such as forceps or a high-frequency knife that is inserted in the channels of the insertion portion 2 can be projected from the distal end of the arms 10 and 11.

Also, as shown in FIGS. 1 and 2, bending portions 10A and 11A that are constituted by a plurality of joint rings 13 being coupled so as to be aligned side-by-side in the axial direction are provided in the arms 10 and 11, respectively. Each bending portion 10A and 11A is connected with the operating portion 4 by a transmission member consisting of a wire and a rod, and so can be bent by operating the operating portion 4. This point shall be explained later.

The operating portion 4 for operating the arms 10 and 11 is provided with a first operating portion 14 for operating the arm 10 and a second operating portion 15 for operating the arm 11. The operating portions 14 and 15 are respectively provided with link operation portions 14A and 15A for operating the link portion 12 and bending operation portions 14B and 15B for operating the bending portions 10A and 11A, respectively. The structure of the link operation portions and the bending operation portions shall be explained later.

Figure 3:
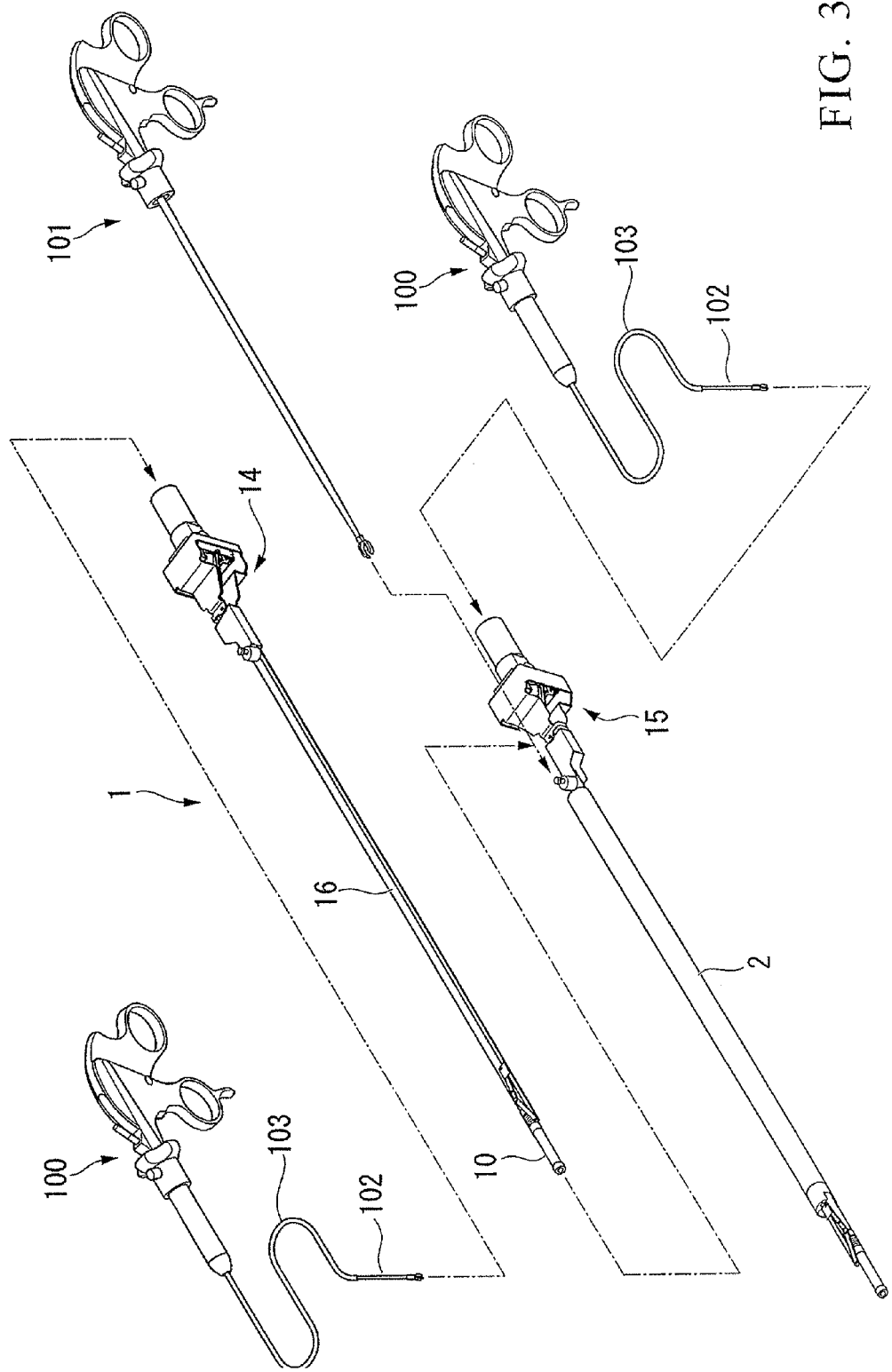
FIG. 3 is a drawing that shows the constitution of the medical manipulator.

In the manipulator 1, as shown in FIG. 3, various kinds of treatment instruments 100 described above are used by being inserted in the first operating portion 14 and the second operating portion 15. Also, one arm 10 is connected with the first operating portion 14 via an inner sheath 16 that is inserted through one channel of the insertion portion 2. Accordingly, as shown in FIG. 3, since the arm 10 and the first operating portion 14 are detachable with respect to the insertion portion 2, the arm 10 and the first operating portion 14 can be removed from the insertion portion 2, and instead a treatment instrument 101 with a rigid insertion portion that is used in normal laparoscopic surgery can be inserted in the channel of the insertion portion 2 and used.

Figure 4:
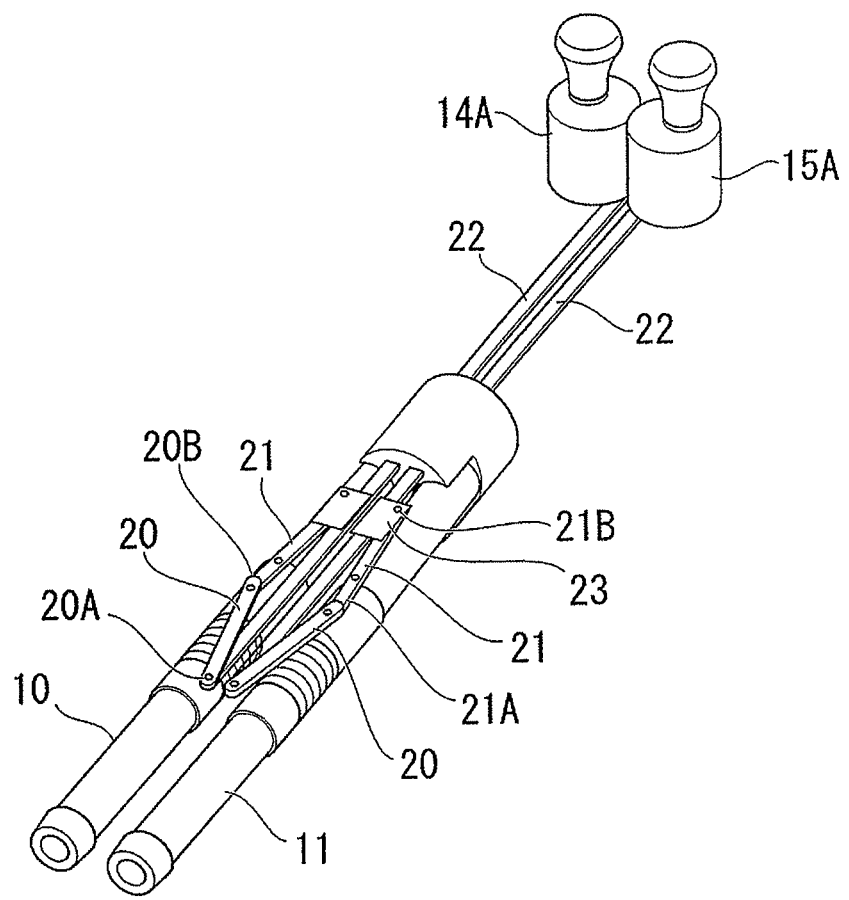
FIG. 4 is a drawing that shows the connection of a link portion and link operation portions of the medical manipulator.

FIG. 4 is a drawing that shows the connection of the link portion 12 and the link operation portions 14A and 15A. Note that the insertion portion 2 is not included in order to make the drawing clearly understandable. The link portion 12 is constituted from a first link 20 on the distal end and a second link 21 on the base end. The pair of the first link 20 and the second link 21 is attached to each of the arms 10 and 11.

A distal end 20A of the first link 20 is rotatably supported by the distal end of a rigid link rod 22 that connects the link portion 12 and the link operation portions 14A and 15A. Meanwhile, a base end 20B of the first link 20 is rotatably supported by the outer periphery surface of the arms 10 and 11 further to the base end than the bending portions 10A and 11A.

A distal end 21A of the second link 21 is rotatably supported by the base end 20B of the first link 20. Meanwhile, the base end 20B of the first link 20 is rotatably supported by a sliding member 23. The sliding member 23 is supported on a link rod 22 and the sliding member 23 and the base end 21B of the first link 20 are capable of sliding over a given range in the lengthwise direction of the link rod 22.

By the aforementioned constitution, when the link operation portions 14A and 15A have been sufficiently pushed out to the arms 10 and 11, as shown in FIG. 4, the arms 10 and 11 become parallel with the axial line of the insertion portion 2 and assume a linear shape as a whole, and therefore are suited to insertion into a body cavity.

Figure 5:
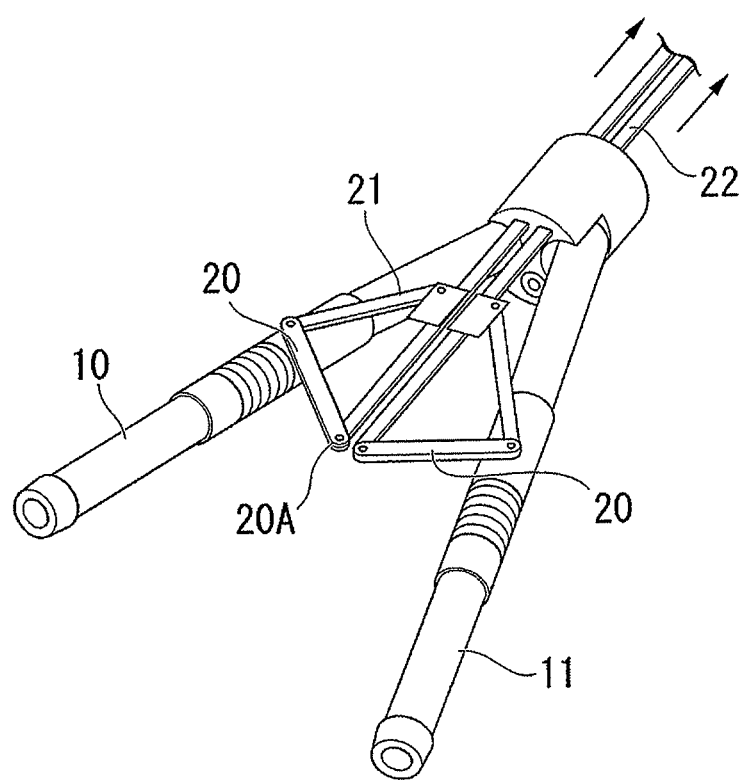
FIG. 5 is a drawing that shows the state of the same link portion in an opened state.

When the link operation portions 14A and 15A are pulled toward the operating portion 4, the link rods 22 that are connected to the link operation portions 14A and 15A are pulled to the operating portion 4. As a result, the distal end 20A of the first link 20 moves to the operating portion 4, and as shown in FIG. 5, the arms 10 and 11 form a predetermined angle with respect to the insertion portion 2, and the distal end portions of the arms 10 and 11 open so as to mutually separate, and so assume a positional relationship that facilitates performance of a procedure.

Figure 6A:
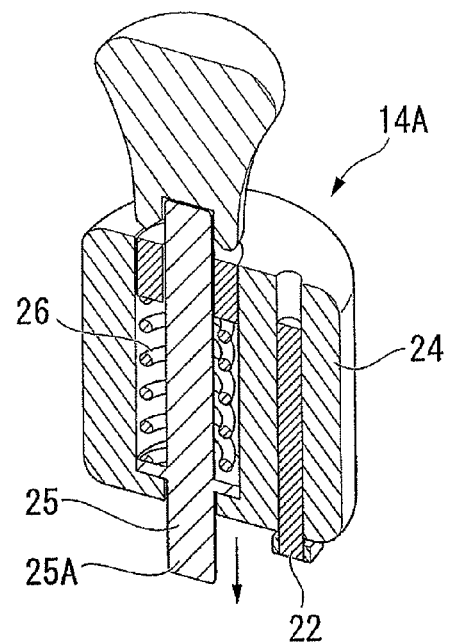
FIG. 6A and FIG. 6B are cross-sectional views of the same link operation portion.
Figure 6B:
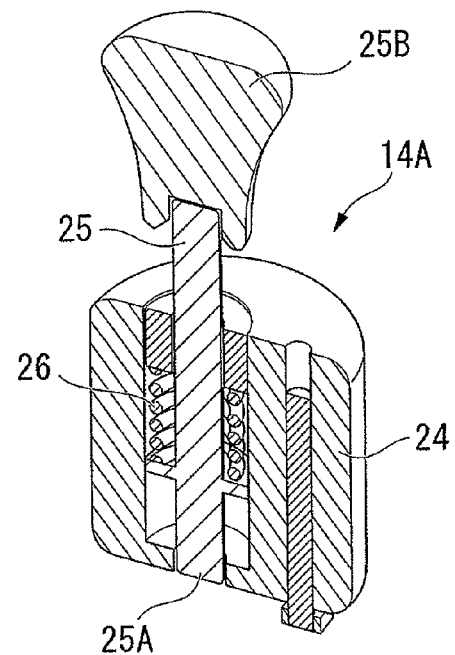

FIG. 6A and FIG. 6B are cross-sectional views that show the link operation portion 14A. The link operation portion 14A is provided with a main body 24 to which the base end of the link rod 22 is fixed, a lever 25 that is inserted in the main body, and a biasing member 26 that biases the lever 25 to the insertion portion 2.

A hole (not illustrated) that a lower end 25A of the lever 25 is capable of fitting in is formed at a predetermined position on the outer periphery surface of the insertion portion 2. When the user pulls the link operation portion 14A to the operating portion 4 in order to open the arms 10 and 11, as shown in FIG. 6A, the lower end 25A of the lever 25 that is biased by the biasing member 26 moves downward and fits in the hole, whereby the arms 10 and 11 are held in the opened state. When returning the arms 10 and 11 to the parallel state, by grasping and pulling up a knob 25B of the lever as shown in FIG. 6B, the fitting of the lower end 25A and the hole of the insertion portion 2 is released.

Note that the link operation portion 14A has the same structure as the link operation portion 14A except for the fixing position of the main body and the link rod.

Figure 7:
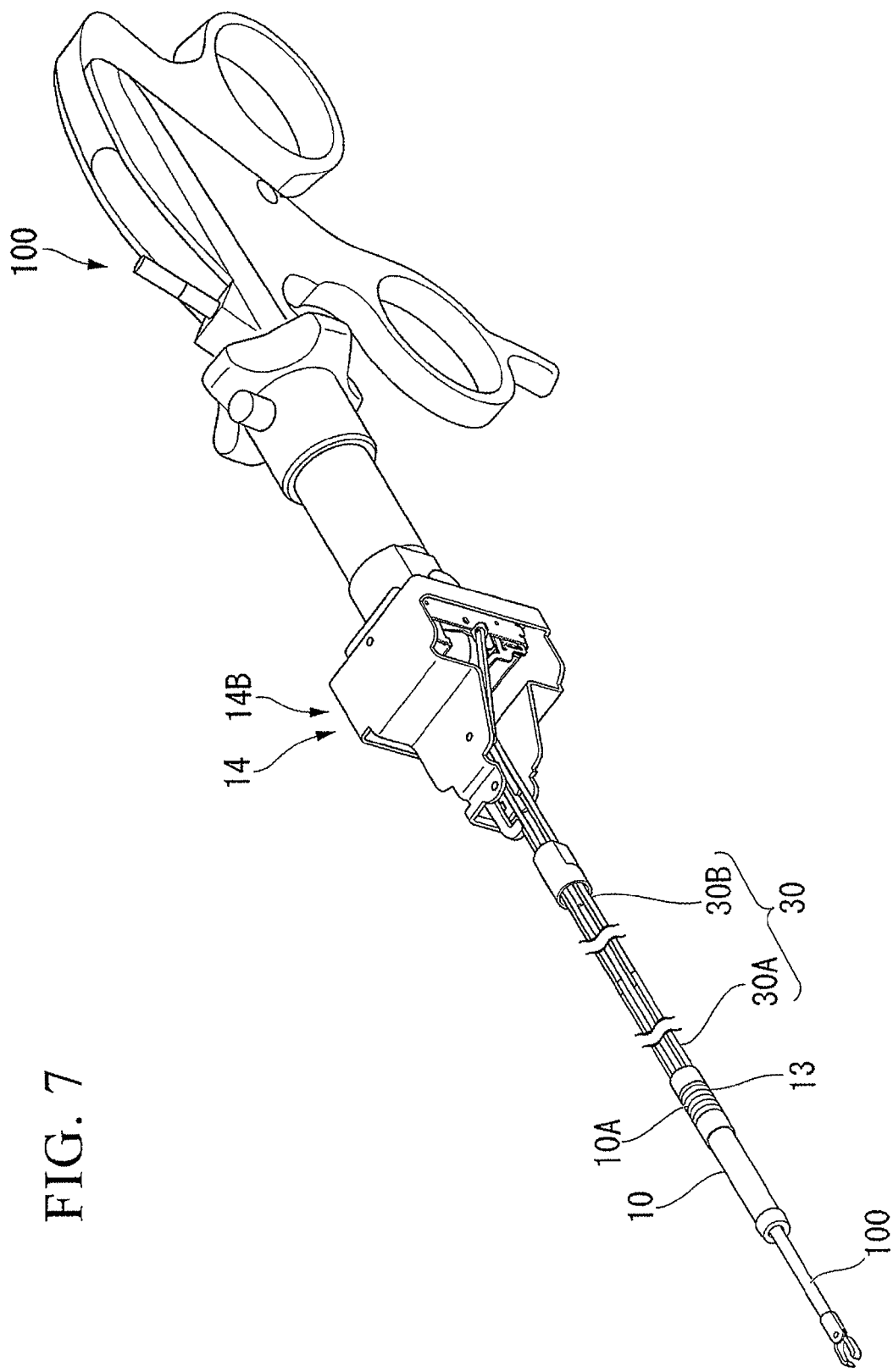
FIG. 7 is a drawing that shows the connection between a bending portion of an arm and a bending operation portion of a first operating portion in the manipulator.

FIG. 7 is a drawing that shows the connection between the bending portion 10A of the arm 10 and the bending operation portion 14B of the first operating portion 14. Note that the insertion portion 2 is not included similarly to FIG. 4.

A transmission member 30 that connects the joint rings 13 of the bending portion 10A and the bending operation portion 14B is divided into the two regions of a first region 30A on the joint rings 13 side and a second region 30B on the bending operation portion 14B side.

The first region 30A extends from the joint rings 13 by a predetermined length, for example, a few centimeters, beyond the base end of the arm 10. The first region 30A is formed with a material that has flexibility such as wire or the like so as not to interfere with the operation of opening the arm 10 described above. The second region 30B that is connected to the base end portion of the first region 30A and extends to the vicinity of the bending operation portion 14B is formed with a rigid material such as a rod and efficiently transmits the operation of the bending operation portion 14B to the arm 10.

Four transmission members 30 are attached at every rotation angle of 90° about the axial line to the outer periphery surface of the joint rings 13 that are furthest to the distal end. Accordingly, by moving the bending operation portion 14B in the direction up/down or left/right viewed from the base end (hereinafter, described simply as up/down or left/right directions), the user can bend the bending portion 10A and move the region of the arm 10 further to the distal end than the bending portion 10A in the desired direction up/down or left/right. Note that the bending operation portion 15B has the same structure.

Figure 8:
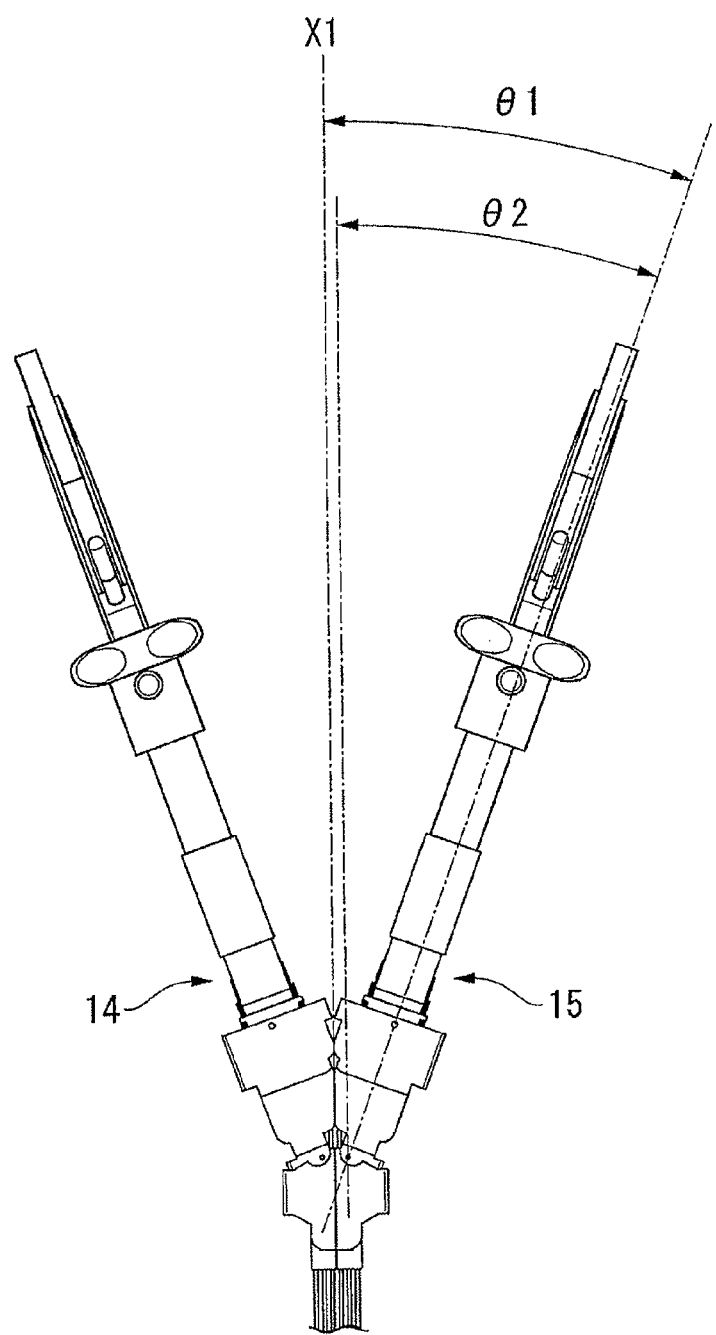
FIG. 8 is a drawing that shows an operating portion of the manipulator.

It is possible to hold the first operating portion 14 and the second operating portion 15 in the state of forming a predetermined angle $\theta_1$ with respect to the axial line $X_1$ of the insertion portion 2 as shown in FIG. 8. Since the maximum swing angle $\theta_2$ during operation of the operating portions 14 and 15 is set to be the angle $\theta_1$ or less, even if the operating portions 14 and 15 are operated to approach each other, the operating portions 14 and 15 and the operating portion of the treatment instrument 100 that is inserted will not interfere.

The four transmission members 30 and the bending operation portions 14B and 15B are connected so as to be able to smoothly perform operation of the bending portion even if the operating portions 14 and 15 are held in a state of forming an angle $\theta_1$ with respect to the insertion portion 2. Hereinbelow, a detailed explanation shall be given using the bending operation portion 14B as an example.

Figure 9A:
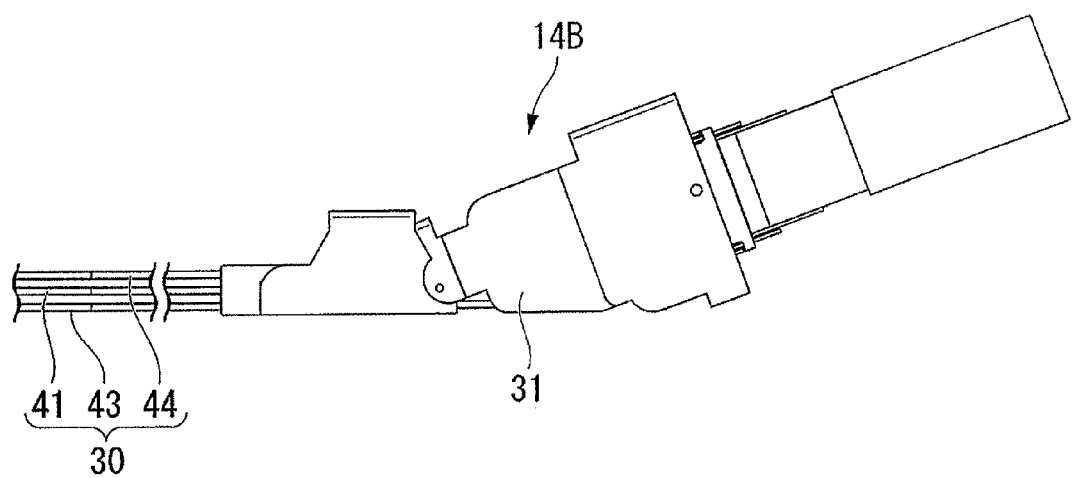
FIG. 9A is a plan view that shows a connection part of the bending operation portion and transmission members when the first operating portion is held in a state of forming a predetermined angle with respect to the insertion portion.
Figure 9B:
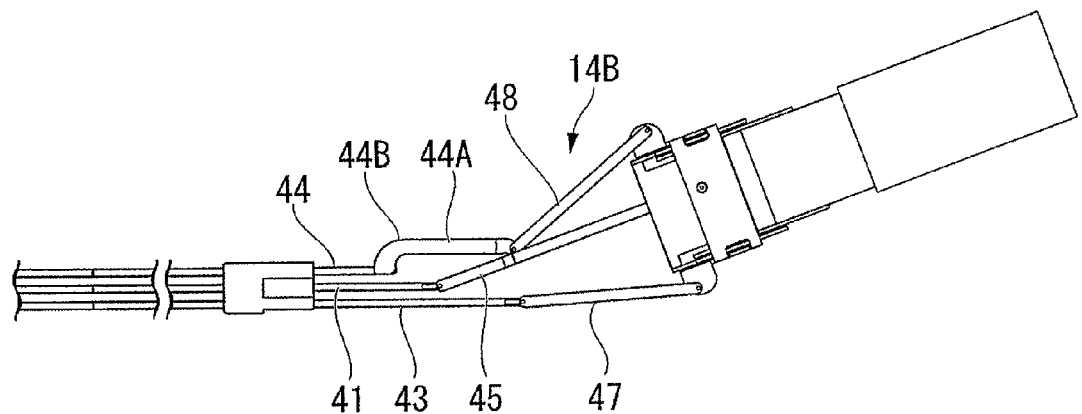
FIG. 9B is the drawing of FIG. 9A without a cover.
Figure 10A:
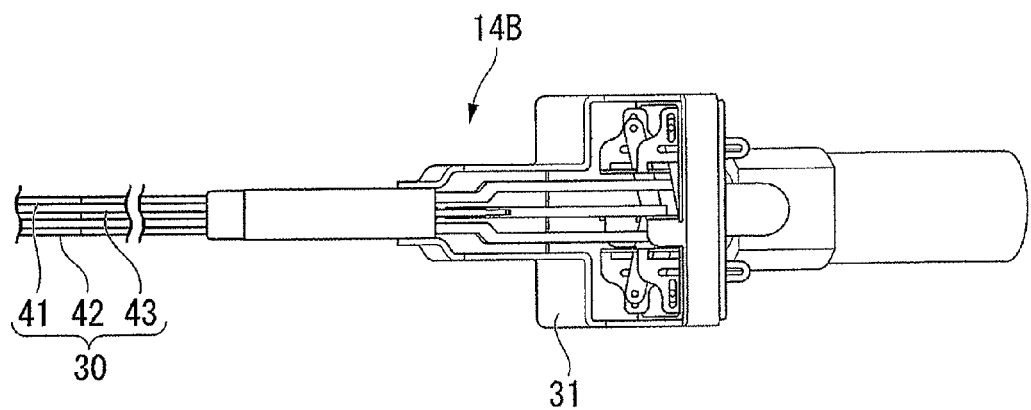
FIG. 10A is a front view that shows the connection part of the bending operation portion and the transmission members when the first operating portion is held in a state of forming a predetermined angle with respect to the insertion portion.
Figure 10B:
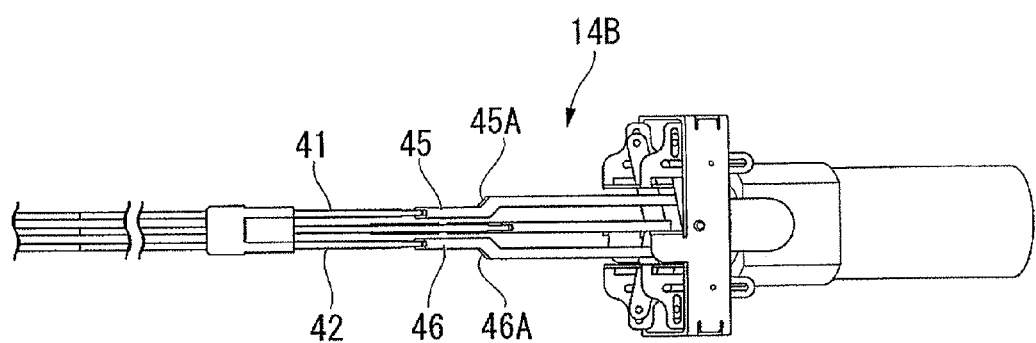
FIG. 10B is the drawing of FIG. 10A without the cover.

FIG. 9A and FIG. 10A are a plan view and a front view, respectively, that show the connection part of the bending operation portion 14B and the transmission members 30 when the first operating portion 14 is held in a state of forming an angle $\theta_1$ with respect to the insertion portion 2. FIG. 9B and FIG. 10B are drawings that show the state of a cover 31 that covers the connection part removed from FIG. 9A and FIG. 10A, respectively. The bending operation portion 14B is supported so as to be able to swing in the left/right direction with respect to the cover 31.

Four transmission members 41, 42, 43, and 44 are all connected with the bending operation portion 14B via an operating portion link described below.

As shown in FIG. 9B and FIG. 10B, the base end of the first transmission member 41 for bending the bending portion 10A upward and the second transmission member 42 for bending the bending portion 10A downward are pivoted to relatively rotate in the horizontal direction by the distal end of the first operating portion link 45 and the second operating portion link 46, respectively. The operating portion links 45 and 46 have steps 45A and 46A, respectively, and so are connected to the bending operation portion 14B in the state of the distance between the operating portion links 45 and 46 being greater at the base end portion than the distal end portion. Thereby, interference is prevented with the third transmission member 43 for bending the bending portion 10A leftward and the fourth transmission member 44 for bending the bending portion 10A rightward, as well as the third operating portion link 47 that is connected to the third transmission member 43 and the fourth operating portion link 48 that is connected to the fourth transmission member 44. Also, a step 44B is provided in the vicinity of an end portion 44A of the fourth transmission member 44. The end portion 44A is separated from the end portion of other transmission members by the step 44B, and prevents interference between the fourth operating portion link 48 and other operating portion links.

Figure 11:
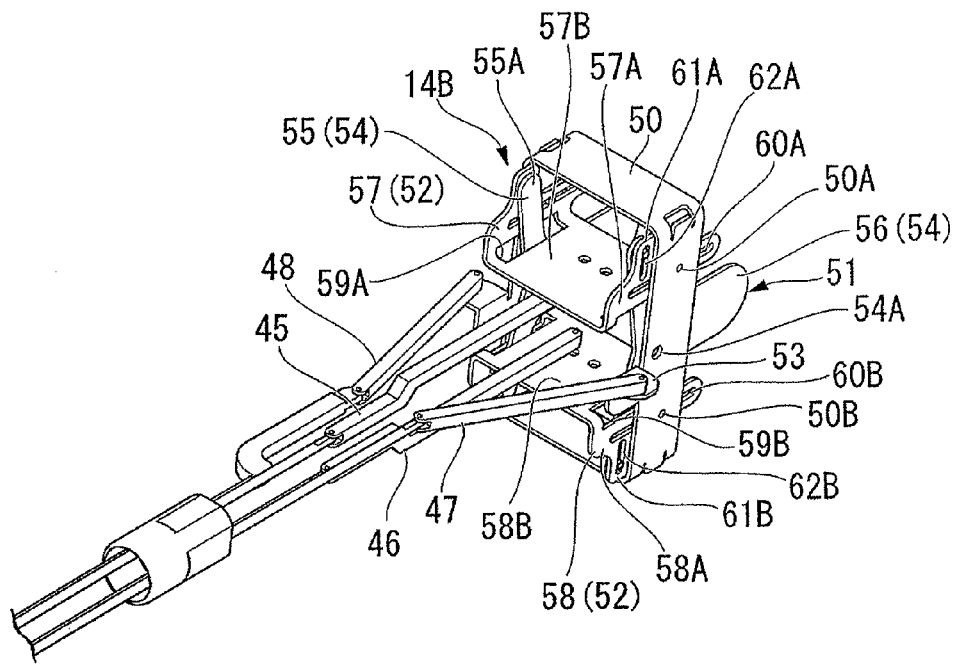
FIG. 11 is a perspective view of the bending operation portion.

FIG. 11 is a perspective view of the bending operation portion 14B. The bending operation portion 14B is provided with a frame body 50 to which the base ends of the third operating portion link 47 and the fourth operating portion link 48 are connected, a swing member 51 that is attached to the frame body 50 in a freely rotating manner, and a pair of sliding members 52 that are attached to the swing member 51.

The frame body 50 is a cylindrical member with an approximately square shape, and has a pair of tongue pieces 53 that project out right and left. The end portions of the third operating portion link 47 and the fourth operating portion link 48 are connected to the tongue pieces 53 so as to mutually separate and to be capable of turning in the horizontal direction with respect to the frame body 50 (a direction parallel with the aforementioned horizontal direction).

The swing member 51 is constituted by two Y-shape members 54 being disposed in parallel and coupled so as to be incapable of relative movement. The swing member 51 is inserted in the frame body 50 so that the Y-shaped members 54 are parallel with the left and right wall surfaces of the frame body 50, and a center portion 54A of each Y-shaped member 54 is rotatably pivoted on the left and right wall surfaces of the frame body 50. Thereby, two legs of the Y-shape of each Y-shaped member of the swing member 51 project forward, while the remaining leg projects rearward. Hereinbelow, a section of the frame body 50 that projects forward is called a front portion 55, and a portion of the frame body 50 that projects rearward is called a back portion 56. The pair of sliding members 52 consists of a first sliding member 57 that is arranged on the upper side in the frame body 50 and a second sliding member 58 that is arranged on the lower side. The sliding members 57 and 58 are members with an approximate U-shape in which both ends are plate-shaped members that are folded at an approximate right angle, and respectively have vertical portions 57A and 58A that are folded at right angles and a horizontal portion 57B and 58B that is between the vertical portions at both ends.

The first sliding member 57 and the second sliding member 58 are inserted in the frame body 50 with the vertical portions 57A of the former facing upward and the vertical portions 58A of the latter facing downward. The base end of the first operating portion link 45 is fixed to the horizontal portion 57B, and the base end of the second operating portion link 46 is fixed to the horizontal portion 58B. The base ends of the first operating portion link 45 and the second operating link 46 are rotatable in the horizontal direction with respect to the first sliding member 57 and the second sliding member 58.

Two each of cutaway portions 59A and 59B that are respectively parallel with the vertical portions 57A and 58A are provided at regions of the horizontal portions 57B and 58B of the sliding members 57 and 58 in the vicinity of the vertical portions 57A and 58A. Upper end portions 55A of the front portion 55 are inserted through the cutaway portions 59A, and lower end portions 55B (refer to FIG. 13A) are inserted through the cutaway portions 59B. The front portion 55 is capable of sliding over a given range within the cutaway portions 59A and 59B.

The vertical portions 57A and 58A respectively have sliding grooves 60A and 60B that are formed in parallel with the horizontal portions 57B and 58B and convex portions 61A and 61B of which a portion projects out so as to separate from the horizontal portions 57B and 58B.

Protrusions 50A and 50B that project from the wall surface of the frame body 50 to the inside are respectively inserted in the sliding grooves 60A and 60B. Slot holes 62A and 62B that extend so as to be approximately perpendicular with the horizontal portions 57B and 58B are formed in the convex portions 61A and 61B. The upper and lower end portions 55A and 55B of the front portion 55 that are inserted in the cutaway portions 59A and 59B are engaged with the slot holes 62A and 62B by a pin or a hinge or the like. That is, the upper and lower end portions 55A and 55B of the front portion 55 are capable of sliding in the slot holes 62A and 62B, respectively.

The operation of the bending operation portion 14B constituted as mentioned above shall be described.

Figure 12:
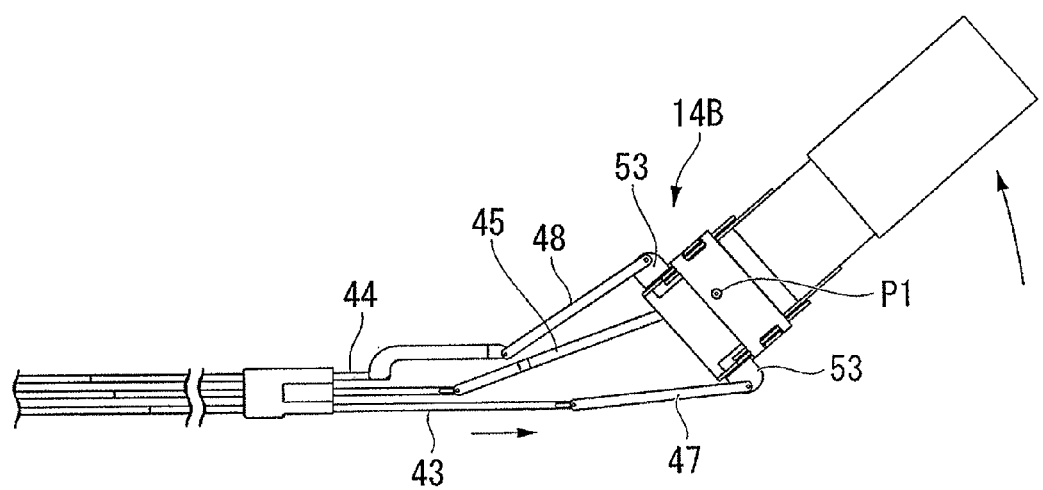
FIG. 12 is a drawing that shows the state of the base end of the bending operation portion having moved to the right.

FIG. 12 is a drawing that shows the state of the base end of the bending operation portion 14B having moved to the right. By the movement of the bending operation portion 14B, the third transmission member 43 is pulled to the base end via the third operating portion link 47. In this way, the bending portion 10A of the arm 10 bends to the left side. The base ends of the third operating portion link 47 and the fourth operating portion link 48 that are pivotally supported by the tongue pieces 53 are positioned further to the distal end of the bending operation portion 14B in the axial line direction than the base ends (position P1 in FIG. 12) of the first operating portion link 45 and the second operating portion link 46 that serve as the swing center with respect to the cover 31 when the bending operation portion 14B is operated in the horizontal direction. For this reason, the pulling amount of the third transmission member 43 and the fourth transmission member 44 is increased during horizontal direction operation, and it is possible to efficiently perform the bending operation with a small stroke (operation amount of the bending operation portion). Note that at this time, the first transmission member 41 and the second transmission member 42 do not advance or retreat. Also, the operation when the base end of the bending operation portion 14B has moved to the left is nearly the same.

Figure 13A:
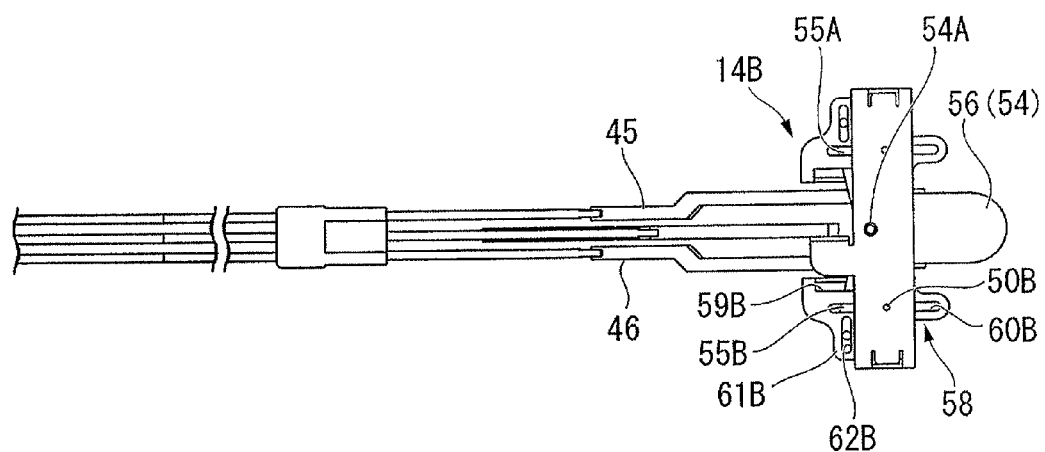
FIG. 13A is a front view of the bending operation portion 14B in which the bending portion is in a horizontal state.
Figure 13B:
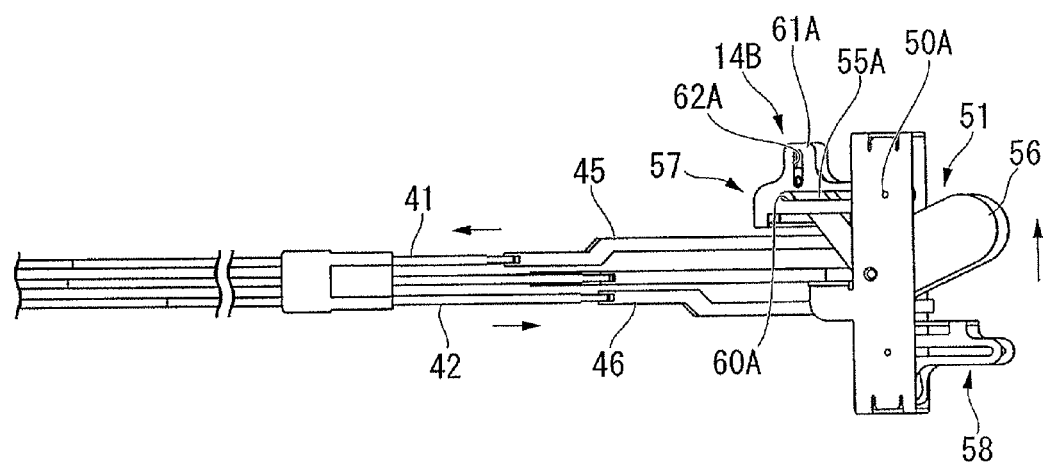
FIG. 13B is a drawing that shows the state of the base end of the bending operation portion having moved up from the state of FIG. 13A.

FIG. 13A is a front view of the bending operation portion 14B in which the bending portion 10A is in a horizontal state, and FIG. 13B is a drawing that shows the state in which the base end of the bending operation portion 14B has moved up. Due to the movement of the base end of the bending operation portion 14B, the back portion 56 of the swing member 51 moves upward. In accordance with that, as shown in FIG. 13B, the lower end portion 55B of the front portion 55 moves to the base end. The lower end portion 55B slides within the cutaway portion 59B, and after abutting the rear end of the cutaway portion 59B, pushes the second sliding member 58 and causes it to move to the base end.

At this time, the lower end portion 55B also moves downward along with moving to the base end, but since the lower end portion 55B slides in the slot hole 62B that is formed in the convex portion 61B, the downward movement is not transmitted to the second sliding member 58. Moreover, since the protrusion 50B is inserted in the sliding groove 60B, the second sliding member 58 is moved to the base end without moving in the vertical direction. Similarly, the first sliding member 57 is pushed by the upper end portion 55A and moved to the distal end without moving in the vertical direction.

By doing so, the second transmission member 42 is pulled to the base end, and the first transmission member 41 is pushed to the distal end, whereby the bending portion 10A is bent downward. In the vertical direction operation, the upper and lower end portions 55A and 55B that serve as substantive support points of the first operating portion link 45 and the second operating portion link 46, in the state shown in FIG. 13A of the bending portion 10A being horizontal, are positioned further to the distal end in the axial line direction of the bending operation portion 14B than the center portion 54A of each Y-shaped member 54 that serves as the swing center of the bending operation portion 14B. Accordingly, as well as during a horizontal direction operation, the pulling amount of the first transmission member 41 and the second transmission member 42 is increased during vertical direction operation, and it is possible to efficiently perform the bending operation with a small stroke (operation amount of the bending operation portion).

As stated above, the further the turning support points of the links 45 to 48 are positioned to the distal end than the swing center of the bending operation portion, the smaller the operation stroke can be made. However, accompanying that, when the operation force amount and operation stroke that occur when moved a given angle, for example, 300 from the neutral state of the bending portion differ between the links 45 to 48, the operational feeling of the user changes depending on the direction, which leads to a drop in operability. In the manipulator 1 of the present embodiment, in consideration of this point, the positions of the turning support points of the links 45 to 48 are decided so that the operation force amount and operation stroke per unit operation amount in each link become generally the same. This kind of optimization can be performed by examining through experiments and the like the relationship between the torque that is input by operation in each direction of the bending operation portion and the output force amount.

The treatment instrument that is used by insertion in the manipulator 1 may be a typical endoscope whose insertion portion has flexibility, but when using an treatment instrument that is constituted so that the distal end portion of the insertion portion has a rigid portion 102 that is formed with a rigid member or the like of a given length similarly to the treatment instrument 100 shown in FIG. 3, when the arms 10 and 11 are projected out, it is possible to perform a procedure by causing a large force to act on the target tissue.

At this time, when the rigid portion 102 is formed with a smaller diameter than the flexible portion 103 that locates more to the base end, since a given clearance is ensured with the channel of the insertion portion 2 or the inner surface of the inner sheath 16 in which it is inserted, it is possible to smoothly insert the arms 10 and 11.

The diameter of the flexible portion 103 is preferably formed to be generally the same as the inner diameter of the channel of the insertion portion 2 or the inner sheath 16 in which it is inserted. By doing so, since clearance between the flexible portion 103 and the channel or the like in which it is inserted becomes less, it is possible to maintain the rotation operation property about the axial line of the treatment instrument and advance/retreat property at a high level. Furthermore, if inner diameters of at least a part of the lumens are set so that the rigid portion 102 can enter therein and the flexible portion 103 cannot enter therein in the distal portion than the bending portion 10A of the arms 10 and 11, it is possible to preferably prevent the flexible portion 103 from projecting from the distal ends of the arms 10 and 11.

Also, as shown in FIG. 14A, when the treatment instrument 100 is inserted to the manipulator 1 and is advanced up to the limit with respect to the manipulator 1, it is preferable that the flexible portion 103 does not project out and only the rigid portion 102 project out from the arm 10 (or 11). By doing so, since only the rigid portion 102 projects out from the distal end of the arm 10 during use of the treatment system 120, even with a procedure which requires a large operation force amount, it is possible to preferably perform a procedure without the arms 10 and 11 and the rigid portion 102 being bent. On the other hand, when the treatment instrument 100 is advanced to the limit with respect to the manipulator 1, it is necessary for the flexible portion 103 to locate in an area which corresponds to the bending portion 10A. Otherwise, the bending portion 10A is substantially incapable of bending, whereby it is difficult to perform a procedure which requires operation force.

In order to meet the above described conditions, when the base end portion of the rigid portion 102 is made of the flexible portion 103 only, the length of the flexible portion 103 is preferably shorter than a total lumen length L1 from the base end of the bending operation portion 14B (or 15B) to the distal end of the arm 10 and is longer than a total lumen length L2 from the base end of the bending operation portion 14B to the bending portion 10A.

Furthermore, in both cases when the treatment instrument 100 is advanced up to the limit with respect to the manipulator 1 and when the treatment instrument 100 is retracted up to the limit with respect to the manipulator 1, a region of the treatment instrument 100 located in the channel of the insertion portion 2 may be rigid without having flexibility.

Moreover, when the treatment instrument 100 is retracted up to the limit as shown in FIG. 14B, it is possible to perform a bending operation on the arm 10 with the rigid portion 102 in the state of being retracted if the rigid portion 102 does not reach the bending portion 10A. Accordingly, in the case of a treatment instrument in which there is a need to perform a bending operation on the arm, it is preferable that the length of the rigid portion 102 be set to be shorter than the length of the region of the arm 10 which is closer to the distal end than the bending portion 10A, but in the case of a treatment instrument in which there is no need to perform a bending operation on the arm, this point is not required.

Figure 15:
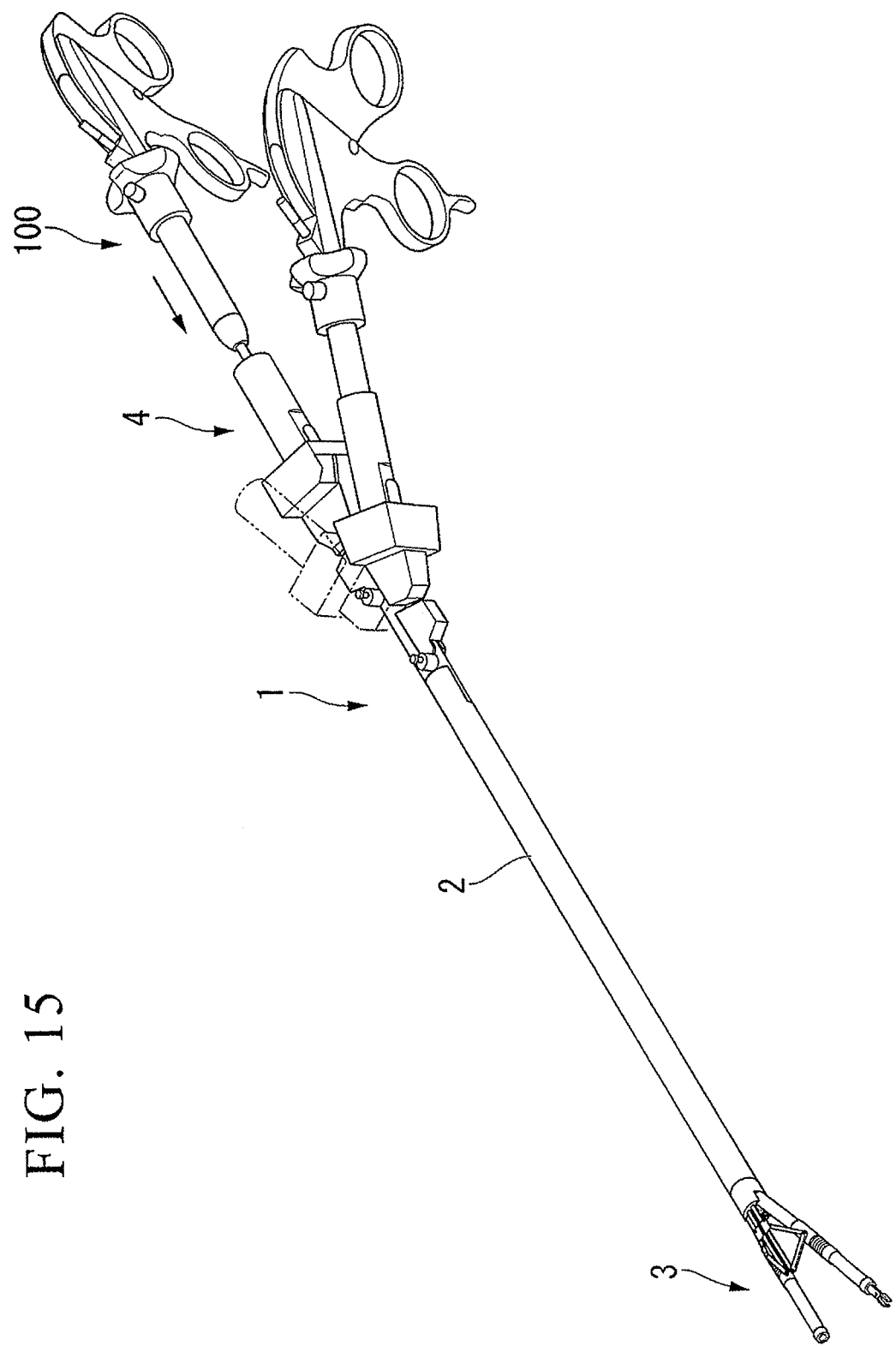
FIG. 15 is a drawing that shows an operation when inserting the treatment instrument in the manipulator.

In the state of the operating portion 4 and the insertion portion 2 forming an angle, since it is not possible to insert a treatment instrument having the rigid portion 102 such as the treatment instrument 100 in the manipulator 1, as shown in FIG. 15, the user inserts the treatment instrument 100 after putting the operating portion 4 in a parallel state with the insertion portion 2. This is also the case when removing the treatment instrument 100 from the manipulator 1.

Figure 16A:
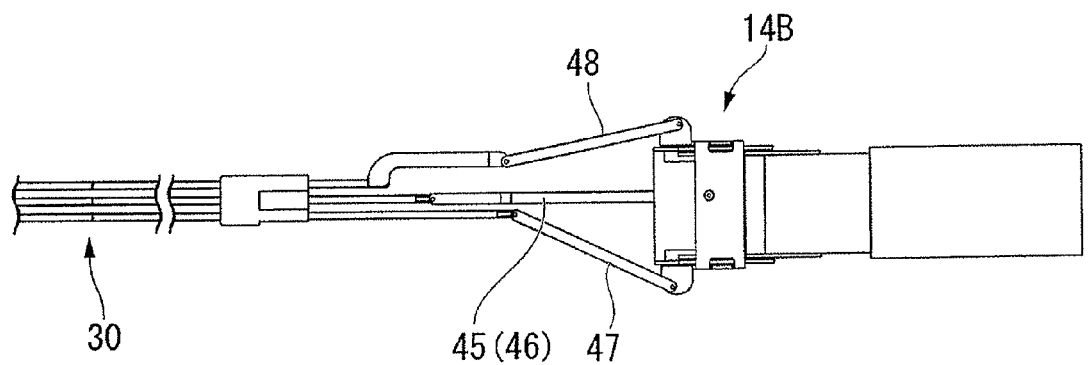
FIG. 16A and FIG. 16B are drawings that show the positional relationship between the bending operation portion and the transmission members.
Figure 16B:
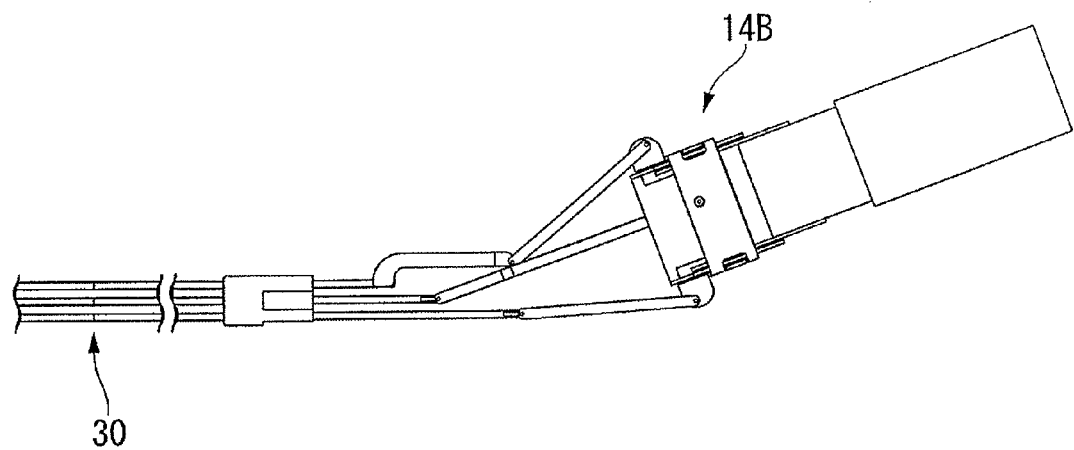

As shown in FIG. 16A, the distal ends of the links 45 and 46 that serve as turning support points when the bending operation portion 14B and the insertion portion 2 are made to form the aforementioned angle of θ1 are disposed on the bisectional line of the distal end support points of the links 47 and 48 when the bending portion 10A is in the linear state. Accordingly, if the bending operation portion 14B is in a neutral state, whether the bending operation portion 14B is in parallel with respect to the insertion portion 2 as shown in FIG. 16A or forming an angle as shown in FIG. 16B, the bending portion 10A is always maintained in a linear state without the positional relationship of the four transmission members 30 changing.

When the manipulator 1 constituted as described above is used, an opening, which is continuous to body cavity such as abdominal cavity or thoracic cavity or the like, is made in an abdominal wall or thoracic wall or the like to insert a trocar, and after performing insufflation as required, the manipulator 1 is inserted in the trocar to be inserted in a body cavity. Then a treatment instrument 100 that is suitably selected in accordance with the type of procedure is inserted from the base end of the bending operation portions 14B and 15B, and the link operation portions 14A and 15A are operated to open the arms 10 and 11 to a shape that facilitates performance of the procedure. Then, while grasping the operating portion of the treatment instrument 100, the bending operation portions 14B and 15B are vertically and horizontally controlled to move the arms 10 and 11 in the desired directions, and then by using the treatment portion at the distal end of the treatment instrument 100 various procedures are performed.

Figure 17A:
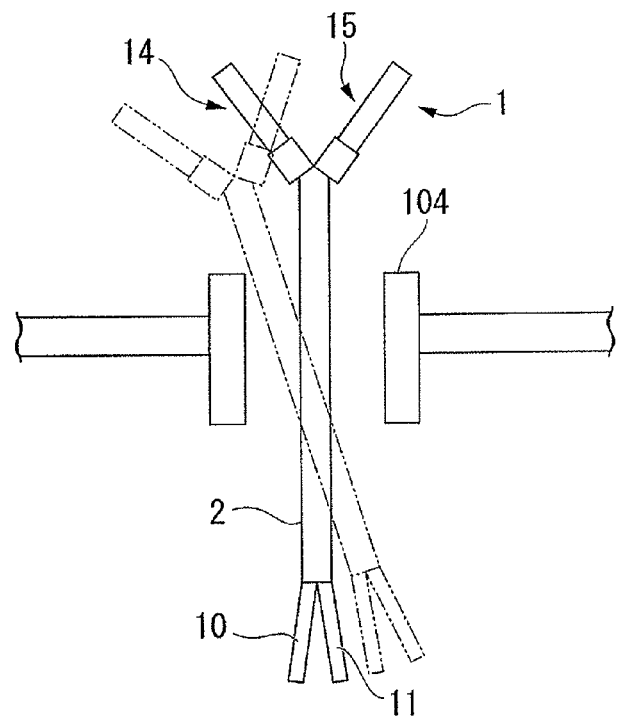
FIG. 17A and FIG. 17B are schematic drawings that show the operation during use of the manipulator.
Figure 17B:
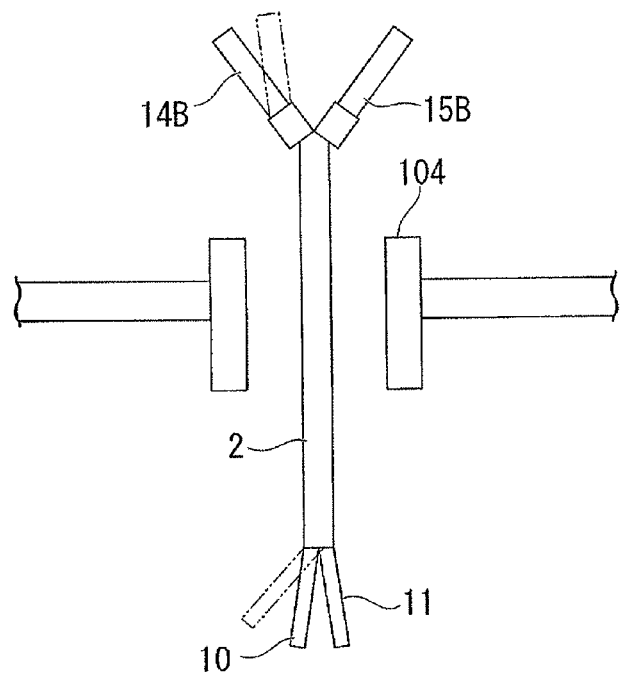

Since the one arm 11 of the manipulator 1 is not detachable from the insertion portion 2, when the operating portions 14 and 15 are moved in the same direction, the operating portions 14 and 15 do not move with respect to the axial line. That is, the bending portions 10A and 11A do not bend. Then, as shown by the schematic drawing in FIG. 17A, the entire manipulator 1 is turned centered on a portion of the insertion portion 2 that is inserted in a trocar 104. In the case of operating a bending portion, as shown in FIG. 17B, while holding the bending operation portion 15B of one arm, for example the arm 11, when the other bending operation portion 14B is operated, the arm 10 can be bent in the desired direction.

Conventionally, in a laparoscopic surgery that is performed by inserting the treatment instrument via trocar 104 or the like, a rigid treatment instrument that does not deform even if a large amount of force is applied is employed. In order to reduce the number of holes to be made in the abdominal wall, it is not impossible to insert a plurality of treatment instruments from a trocar. However, since the insertion portion of the rigid treatment instrument is not flexible, in this case, the plurality of treatment instruments interfere in the trocar or the body cavity, and make the procedure difficult. Accordingly, it is difficult to perform a procedure by inserting a plurality of treatment instruments into a trocar, whereby it is necessary to make one hole per one treatment instrument.

In accordance with the manipulator 1 of the present embodiment, since the manipulator 1 is provided with the arms 10 and 11 which is capable of inserting treatment instruments therein and the photographic device 5, even when the manipulator 1 is inserted to a trocar, it is possible to operate so as not to interfere the plurality of treatment instruments and preferably perform procedures in the body cavity.

Since the distal end portions of the arms 10 and 11 are made of rigid members, they do not bend during procedures. Accordingly, by using the manipulator 1 of the present embodiment as the treatment system 120 in combination with the treatment instrument 100 provided with the rigid portion 102 as described above, it is possible to preferably perform procedures which require a comparatively large amount of force. As a result, even for a difficult procedure, in which an arm portion is bent by a force amount, with a treatment endoscope described in United States Patent Application Publication No. 2007/0249897, it is possible to reliably perform procedures.

Furthermore, since a part of the transmission member 30 which connects the arms 10 and 11 and the operation portion 4 is provided with a rigid second region 30B, a force amount applied by the operation portion 4 is transmitted to the arms 10 and 11 with an attenuation of the force amount applied by the operation portion 4 being inhibited. Accordingly, it is possible to perform procedures by efficiently operating the arms and the treatment instruments inserted to the arms.

Figure 18:
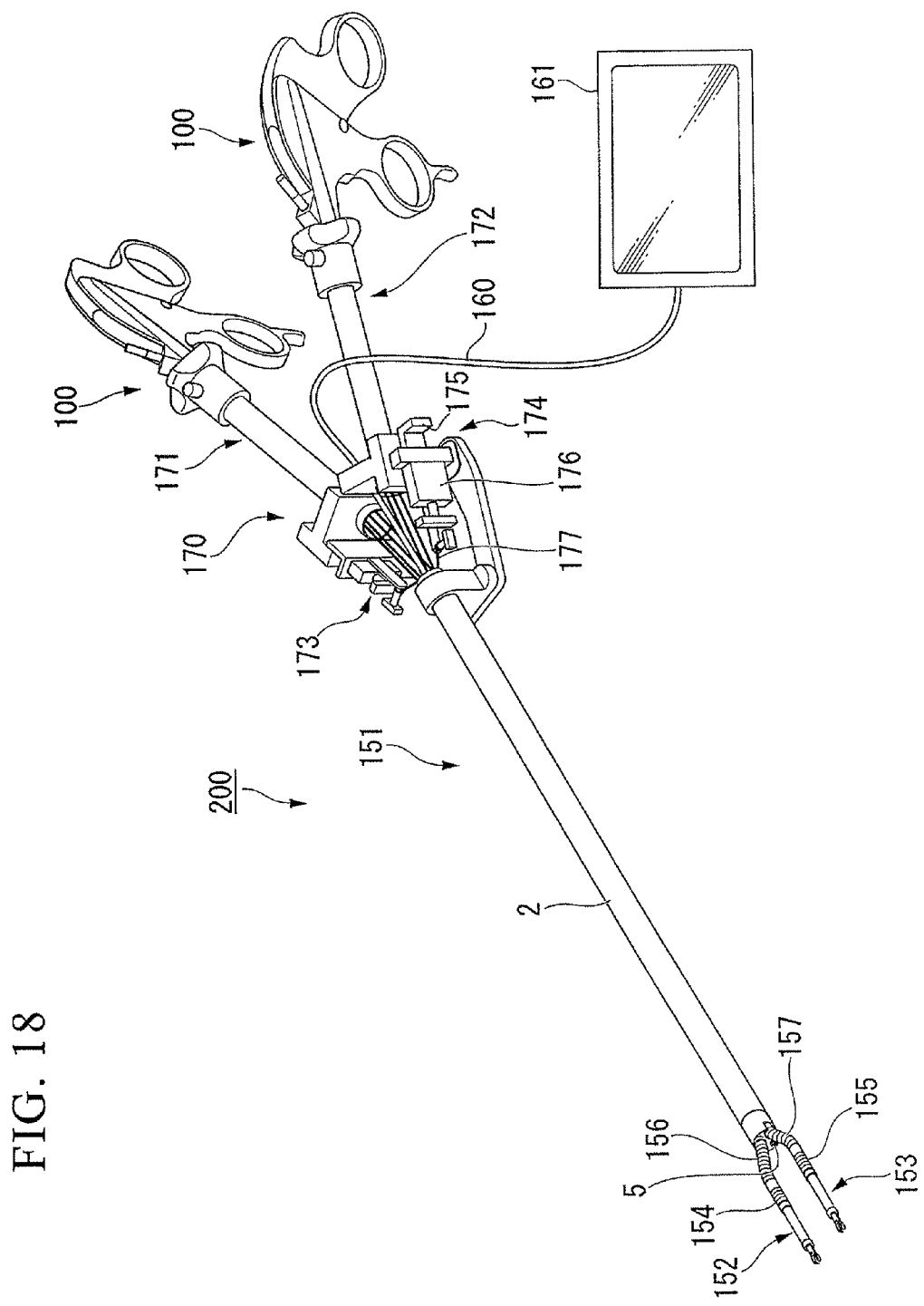
FIG. 18 is a drawing that shows a constitution of a medical manipulator in accordance with a second embodiment of the present invention.
Figure 19:
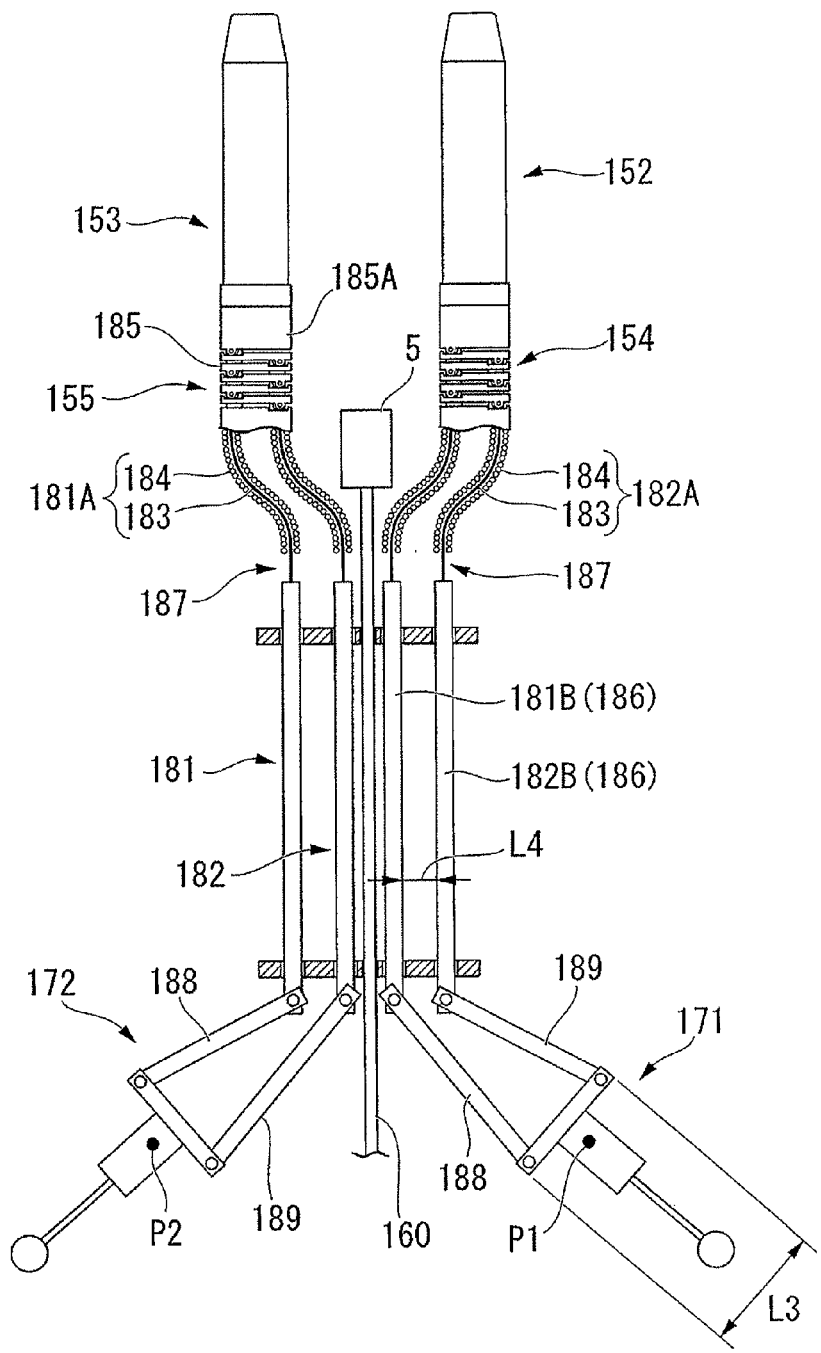
FIG. 19 is a schematic drawing that shows an operation mechanism of the arm of the manipulator.
Figure 20:
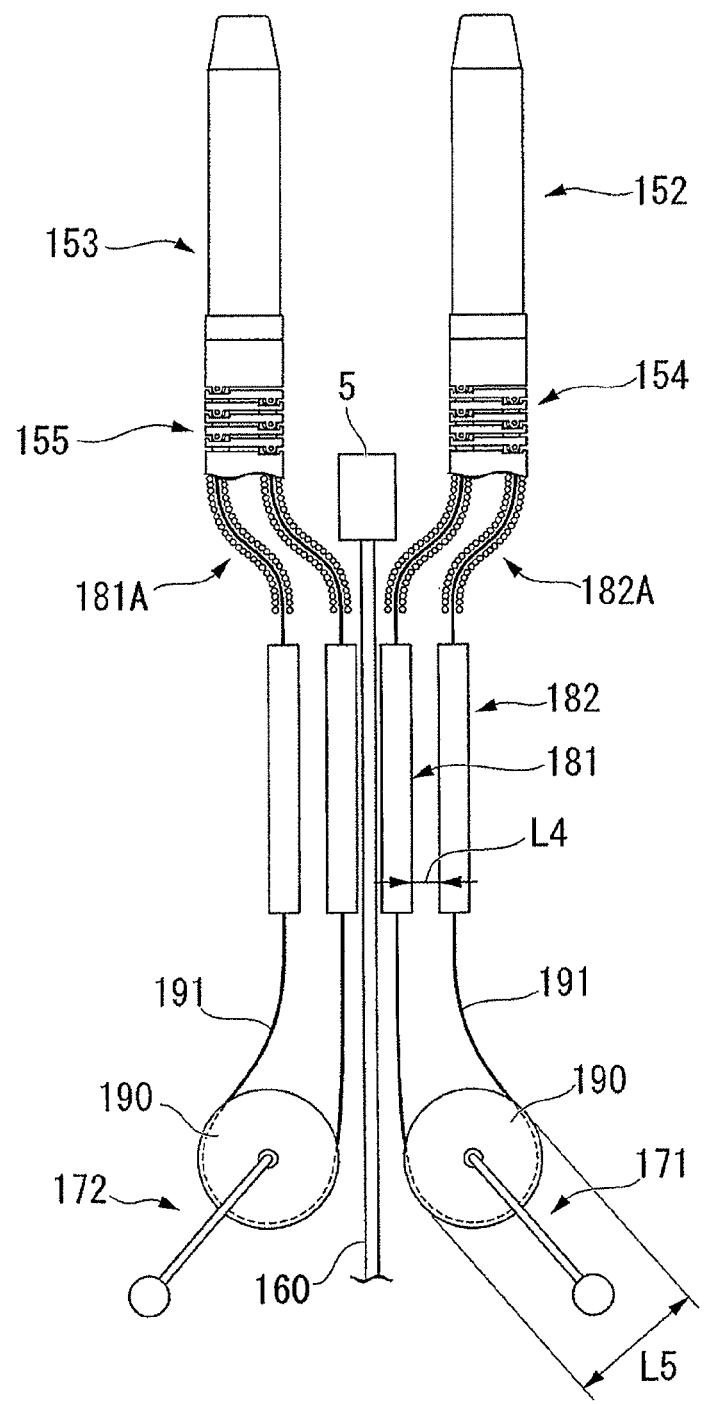
FIG. 20 is a schematic drawing that shows an alternative example of the operation mechanism.

Next, a second embodiment in accordance with the present invention shall be described in reference to FIG. 18 to FIG. 20. Differences between a manipulator 151 of the present embodiment and the above described manipulator 1 are constitutions of the arms and the operation portion. It should be noted that configurations that are similar to those of the previously explained first embodiment will be assigned the same numeric symbol and redundant explanations thereof will be omitted.

FIG. 18 is a general drawing that shows a treatment system 200 which includes a manipulator 151. The photographic device 5 provided at the distal end of the insertion portion 2 is connected to a display portion 161 which includes a conventional image processing device or a monitor or the like by a cable 160 which extends from the base end of the insertion portion 2.

At the distal end of the insertion portion 2, a pair of arms 152 and 153 is provided instead of the arms 10 and 11.

Each of the arms 152 and 153 is provided with first bending portions 154 and 155 for bending the arms in up/down or left/right which have similar configurations as the bending portions 10A and 11A. Furthermore, each of the arms 152 and 153 is provided with second bending portions for making a preferable state for performing procedures (hereinbelow this state is described as "tri-angulation") in which base end portions of each of the arms 152 and 153 are more separated than usual state.

The second bending portions 156 and 157 are configured by a plurality of joint rings being coupled in the axial direction similarly to the first bending portions 154 and 155. Furthermore, similarly to a second bending part provided to a treatment endoscope described in United States Patent Application Publication No. 2007/0249897, by pulling a transmission member connected to the joint rings to an operation portion and holding it, it is possible to hold a bending state of the second bending portions 156 and 157 to form the tri-angulation.

The manipulator 151 is provided with an operation portion 170 instead of the operation portion 4. Bending operation portions 171 and 172 have substantially the same configurations as the bending operation portions 14B and 15B of the first embodiment. However, it should be noted that second bending operation portions 173 and 174 are provided to the manipulator 151 instead of the link operation portions 14A and 15A of the first embodiment.

Each of the second bending operations portions 173 and 174 are provided with a lever 175 and a lock mechanism 176. A transmission member 177 which is connected to the joint rings of the second bending portions 156 and 157 is connected to the lever 175. By pulling the lever 175 to the bending operation portions 171 and 172, it is possible to pull the transmission member 177 and change the shapes of the second bending portions 156 and 157. The lock mechanism 176 has a conventional configuration such as a latchet and is able to hold a pulling state of the lever 157 and the transmission member 177.

FIG. 19 is a schematic drawing that shows a connection between the arms 152 and 153 and the bending operation portions 171 and 172. Here, in order to make the drawing more visible, except for the insertion portion 2, among four of the transmission members for bending the arms 152 and 153, only a third transmission member 181 and a fourth transmission member 182 for bending left/right are shown. The first regions 181A and 182A of the third transmission member 181 and the fourth transmission member 182 are made from a wire 183 and a coil 184 in which the wire 183 is inserted.

A distal end portion of the wire 183 is inserted to each of joint rings 185 of the first bending portions 154 and 155 and is connected to a joint ring 185A which is located in the most distal end by welding or brazing or the like. A base end portion of the wire 183 is connected to a distal end portion of a rod 186 which configures second regions 181B and 182B of each of the transmission members 181 and 182 by welding or brazing or the like. Since the first regions 181A and 182A are flexibly made by the wire 183 and the coil 184, even during tri-angulation where the second bending portions 156 and 157 are fixed in a bending state, operations of the operation portion 170 is preferably transmitted to the first bending portions 154 and 155.

At least a part of the coil 184 is fixed with respect to the arm 183. The length of the coil 184 is set shorter than the length of the wire 183 and an adjustment portion 187 is formed at the base end portion of the coil 184 where a part of the wire 183 is exposed. Functions of the adjustment portion 187 shall be described later.

Bending operation portions 171 and 172 and the rods 186 of each of the transmission members 181 and 182 are connected by a third operation portion link 188 and a fourth operation portion link 189 similarly to the manipulator 1 of the first embodiment. In each of the bending operation portions, a distance L3 between base ends of the third operation portion link 188 and the fourth operation portion link 189 is set longer than a distance L4 between adjacent rods 186.

In the manipulator 151 of the present embodiment configured as described above, by swinging the bending operation portions 171 and 172 left and right with respective swing centers P1 and P2 as their centers, it is possible to bend the first bending portions 154 and 155 of each of the arms 152 and 153 left and right by retracting the transmission members 181 and 182 in longitudinal direction.

The distance L3 between base ends of the third operation portion link 188 and the fourth operation portion link 189 is set longer than the distance L4 between adjacent rods 186. Accordingly, compared to a case in which the distance L3 is configured as a parallel rink as the distance L4, the pulling amount of the transmission member for the same swing amount of the bending operation portions 171 and 172 becomes large. As a result, it is possible to efficiently operate the arms 152 and 153, whereby it is possible to prevent interferences between the bending operations portions during operations.

On the other hand, with the third operation portion link 188 and the fourth operation portion link 189 not being the parallel link, during swinging of the bending operation portions 171 and 172, there will be differences in the pushing and pulling amount of the facing transmission members 181 and 182. Since the adjustment portion 187 where the wire 183 is exposed is provided to each of the transmission members 181 and 182, the generated differences in pushing and pulling amount are absorbed with the wire 183 being bent in the adjustment portion 187. Accordingly, it is possible to preferably operate the arms 152 and 153 with such a problem in which the first bending portions 154 and 155 are uncontrollable being preferably avoided.

In the present embodiment, an example was described in which the adjustment portion 187 is formed with part of the wire 183 being exposed. Instead of this, the adjustment portion may be formed by making a loop of the coil 184 larger and providing such a clearance that the wire 183 can bend in the coil 184. Here, it should noted that by providing the clearance in the coil, it is difficult to make the diameters of the arm and the insertion portion smaller. Therefore, in the case of making the diameters of the arm and the insertion portion smaller, it is preferable to form the adjustment portion by making a part of the wire 183 be exposed.

As shown in an alternative example shown in FIG. 20, the bending operation portions 171 and 172 and each of the transmission members 181 and 182 may be connected by using a pulley 190 and a wire 191. In this case, the adjustment portion may be provided in the wire 191, whereby it is possible to avoid such a problem in which the wire 183 bends on the side of the arms 152 and 153 and touches tissues.

Here, in the case of connecting the bending operation portion and the transmission member by using the pulley 190, by setting the diameter L5 of the pulley 190 to be larger than the above-described distance L4, it is possible to efficiently operate the arms 152 and 153 as the configuration shown in FIG. 19. The first transmission member and the second transmission member that vertically bend the first bending portions 154 and 155 may be connected to the bending operation portions 171 and 172 by using another pulley (not shown). Other than this, the bending operation portion and the transmission member may be connected by using other conventionally known mechanisms such as a chain and a sprocket or a rack and pinion.

Although above described details on the connection between the bending operation portion and the transmission member was not described in the description of the first embodiment, it is possible to employ similar configurations to the manipulator 1 of the first embodiment.

By using the manipulators 1 and 151 configured as described above, it is possible to efficiently perform various procedures which were conventionally performed by using a laparoscope or a thoracoscope. Hereinbelow, a number of patterns shall be described separately referring to FIG. 21 to FIG. 35. It should be noted that the manipulator 1 of the first embodiment is shown as an example of the manipulator of the present invention in the following drawings. However, the manipulator 151 of the second embodiment can be used instead of the manipulator 1 in all the examples. Also, the manipulator 1 and the manipulator 151 may be used in combination.

The first pattern of the various procedures is one in which procedures with respect to two or more different regions in the same body cavity are performed in parallel by multiple people. Here, in the present invention, "region" means a space region capable of performing procedures or the like by using one photographic device. Further details shall be described specifically in explanations on each of the examples.

Figure 21:
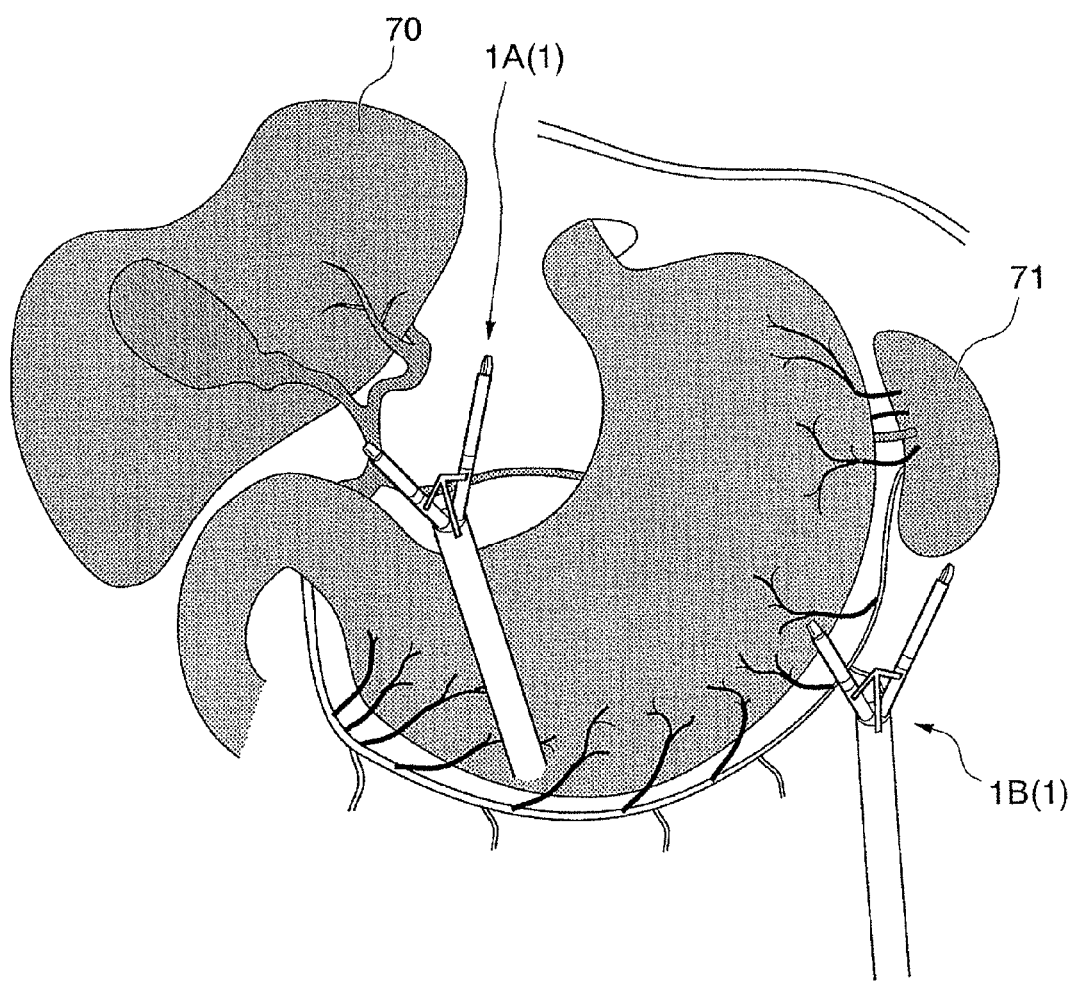
FIG. 21 is a drawing that shows the state of performing a liver and spleen resection using the manipulator.

As one example of a first pattern, one in which procedure with respect to different organs are performed in parallel by multiple people shall be described. FIG. 21 is a drawing that shows the state of performing a liver resection and spleen resection using two of the manipulators 1. The operator who operates one manipulator 1A performs the procedure on the liver 70, and the operator who operates the other manipulator 1B performs the procedure on the spleen 71.

In an ordinary laparoscope-assisted surgery, one trocar is required for each treatment instrument 1, and a trocar is required for inserting the laparoscope. Accordingly, to carry out the procedure shown in FIG. 21, it would be necessary to form five holes in the abdominal wall, thus requiring four or five operators. Also, since there is only one laparoscope serving as an observation device, simultaneously observing the two organs of the liver 70 and the spleen 71 that are comparatively separated from each other is difficult. That is, while one laparoscope captures the liver 70 into view, it is not possible to perform procedures with respect to the spleen 71 and vice versa. Therefore one more laparoscope would be required in order to simultaneously carry out the procedures and the above-described example is a procedure which is performed with respective to two different regions.

According to the manipulator 1 in accordance with the present embodiment, just by opening two holes in the abdominal wall, it is possible to perform the aforementioned procedures with two operators without a problem. Also, since two treatment instruments can be used with one manipulator, it is possible to efficiently perform complicated procedures by inserting a greater number of the treatment instruments than the number of holes made in the body wall (in the aforementioned example, four treatment instruments can be used with two holes). Furthermore, since the manipulator 1 is provided with the photographic device 5 as an observation device, even for organs located in different regions such as the case with the liver 70 and the spleen 71, the operators are capable of carrying out the procedures simultaneously while accurately observing with the photographic device provided with each of the manipulators 1. Accordingly, the surgery time is dramatically shortened, and it is possible to significantly reduce the invasiveness to the patient.

Figure 22:
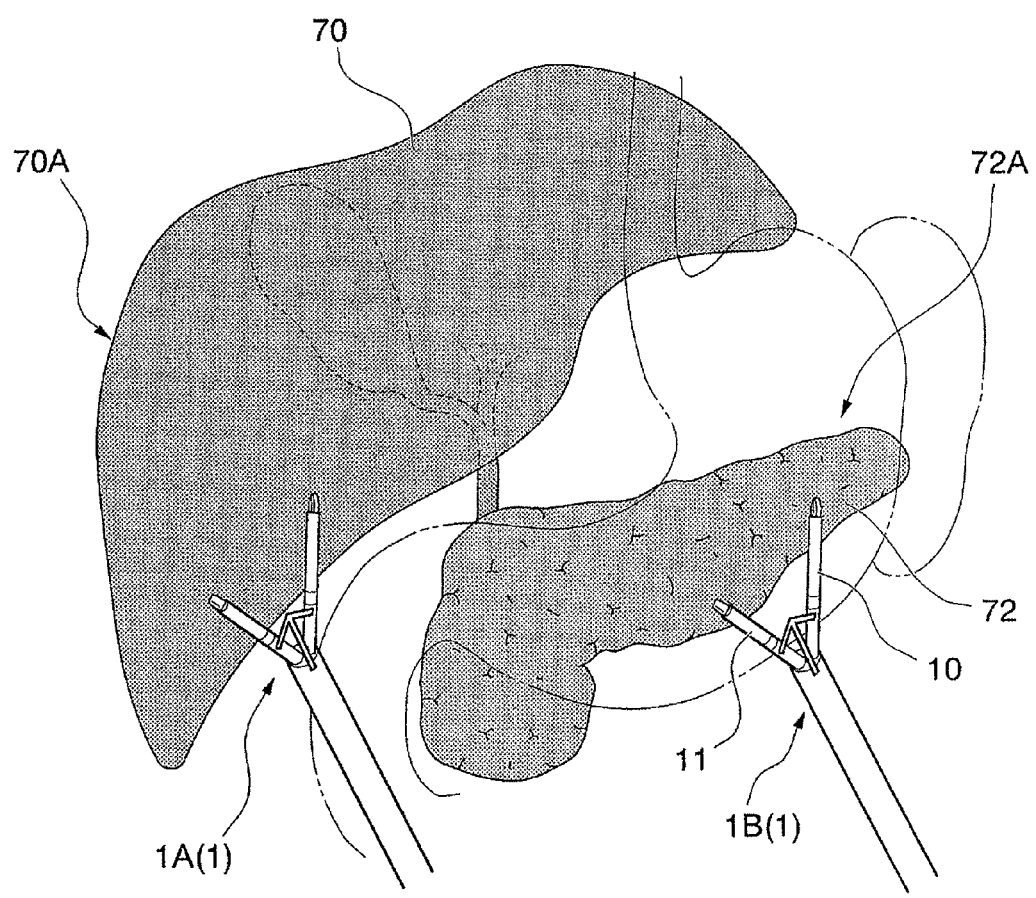
FIG. 22 is a drawing that shows the state of performing a liver and spleen resection using the manipulator.

An example of performing one procedure with several operators is not limited to the liver and spleen of FIG. 21. For example, as shown in FIG. 22, it is possible to carry out resection of the liver 70 and the pancreas 72 simultaneously. Since the liver 70 and the pancreas 72 are located relatively close, in accordance with a specific location for the procedure, it is possible to carry out resection of the liver 70 and the pancreas 72 simultaneously by using one photographic device. In this case, it can be regarded that a plurality of procedures is performed within the same region. However, for example, procedures are performed in a right lobe 70A of the liver 70 and a pancreatic tail 72A of the pancreas 72, since locations of both organs are separated, it is difficult to perform these procedures simultaneously with a field of view of one photographic device. In this case, it can be regarded that procedures are performed in two different regions.

The procedures performed in each of the regions may be a part of the same operation having a common objective or different procedures having different objectives. As an example of the former one is such as a simultaneous carrying out of a hepatectomy of a hepatocellular carcinoma associated with a hepatic cirrhosis and an accompanying lienectomy.

On the other hand, an example of the latter one is such as a simultaneous carrying out of gallbladder extraction and tubal ligation, spleen extraction, appendix resection, and the like, or a simultaneous carrying out of kidney extraction and spleen extraction. By carrying out simultaneously even a plurality of different procedures not having directly common objectives with low invasiveness, it is not necessary to divide those procedures into several procedures with recovery periods between each of the procedures. This contributes to a significant reduction of the burden on the patent.

Note that most of the procedures mentioned above are procedures in which it is necessary to apply a comparatively large force on the tissue. Since the arms 10 and 11 of the manipulator 1 are rigidly constituted without having flexibility except for the bending portions, it is possible to generate the same level of force as a treatment instrument with general rigidity, and so it is possible to carry out these procedures.

The second pattern is one in which a plurality of people carry out a procedure at different regions separated from one another by dividing walls.

In the aforementioned two examples, two different regions locate in the abdominal cavity which is the same body cavity. However, in the second pattern, at least one of the different regions is located in a different body cavity which is separated by a dividing wall from a body cavity where other regions are located therein.

Figure 23:
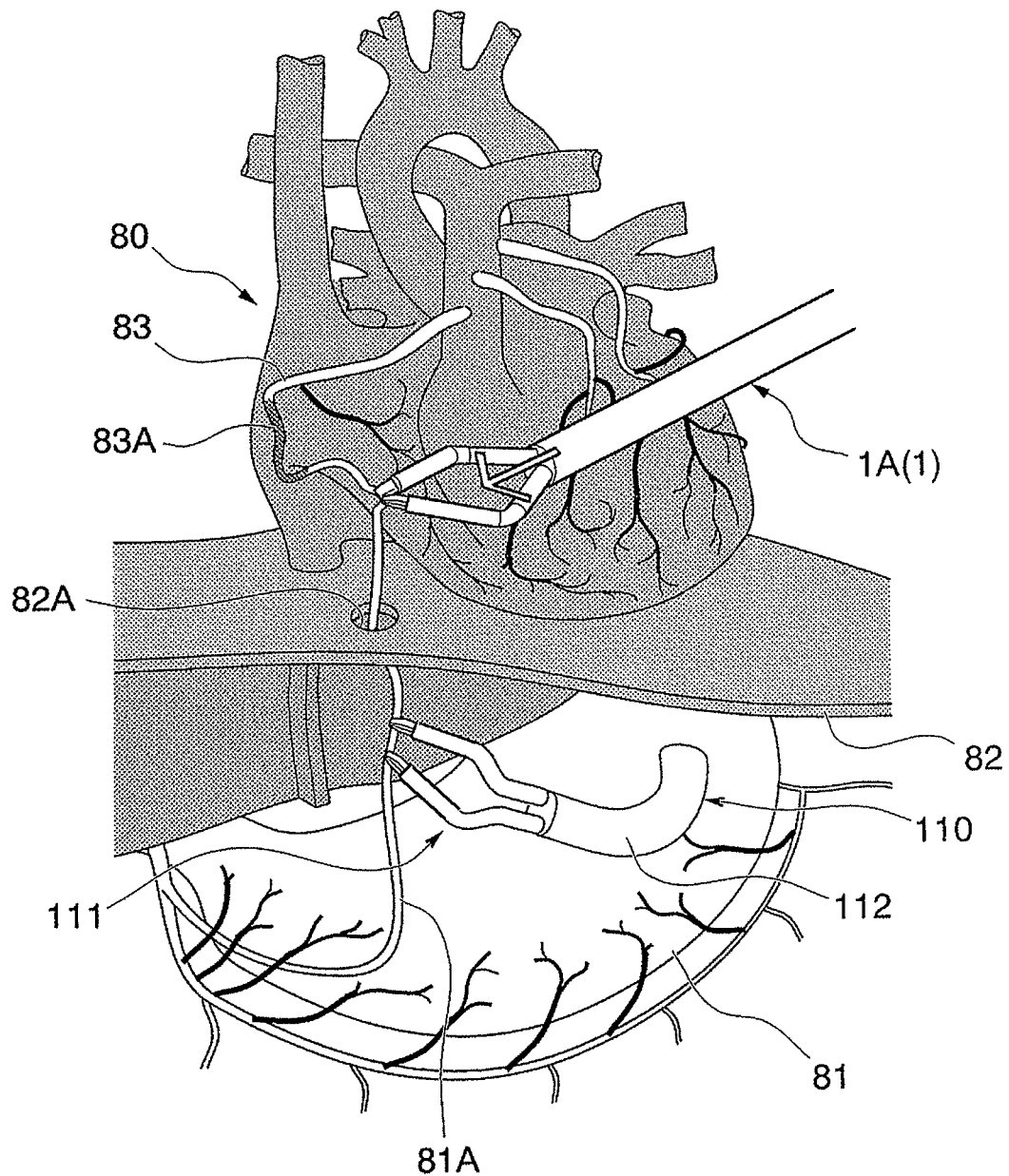
FIG. 23 is a drawing that shows the state of performing a coronary artery bypass graft using the manipulator.

FIG. 23 is a drawing that shows the state of performing a coronary artery bypass graft using the manipulator 1. One operator makes the manipulator 1A enter the thoracic cavity from the thoracic wall and performs preparation work such as pericardiolysis on the heart 80. As an entry path to the thoracic cavity, it is possible to favorably use a gap between the ribs or a region at which the skin is thin near the clavicle.

Another operator causes the manipulator to enter an abdominal cavity, and detaches a blood vessel such as the gastroepiploic artery 81A from the stomach 81 to be used in the bypass formation in parallel with the aforementioned preparation work. Then, the gastroepiploic artery 81A that has been detached from the stomach 81 is passed from a hole 82A that has been opened in the diaphragm 82 to the operator on the thoracic cavity side.

The operator on the thoracic cavity side who has received the gastroepiploic artery 81A connects the gastroepiploic artery 81A to the distal side of the constricted area 83A of the coronary artery 83 to form the bypass, and ensures blood supply to the distal side.

In the coronary artery bypass graft described above, the region to which the manipulator 1 performs a procedure locates in the thoracic cavity and the region to which the other manipulator (treatment endoscope 110 or the like as described later) performs a procedure locates in the abdominal cavity. Since these two regions are separated by the dividing wall which is the diaphragm, it is not possible to simultaneously perform two procedures by using only one of the field of views of the thoracoscope or the laparoscope.

Also, in the case of selecting a gastroepiploic artery as a bypass graft, each of the processes of a single operation named coronary artery bypass graft is performed in two different regions separated by the diaphragm 82. Ordinarily, in order to perform aforementioned procedures, a thoracotomy and laparotomy are required, which takes a long amount of time, and the invasiveness to the patient is great. However, if the manipulator 1 according to the present embodiment is used, it is possible to perform the procedure just by opening one hole each in the thoracic wall and the abdominal wall, and so a thoracotomy and laparotomy are not required. Moreover, since it is possible for both operators to carry out the procedures simultaneously, it is possible to significantly shorten the time required, and it is possible to dramatically reduce the invasiveness to the patient.

Here, in the case of selecting an internal thoracic artery as the bypass graft as well, it is possible to detach the internal thoracic artery from the thoracic wall and perform a preparatory work with respect to the heart simultaneously, whereby it is advantageous.

Note that in the procedure given above, as shown in FIG. 23, as the manipulator on the abdominal cavity side, the treatment endoscope 110 as disclosed in U.S. Patent Application Publication No. 2007/0249897 may be used. Since this treatment endoscope 110 is constituted by two arm portions 111 that are capable of a bending operation being attached to the distal end of an insertion portion 112 that has flexibility, it is possible to insert it from a natural orifice such as the mouth, and possible to introduce a treatment instrument into the abdominal cavity via the stomach 81 as shown in FIG. 23.

Since only a treatment instrument having flexibility can be inserted in the treatment endoscope 110, it is difficult to cause a large force to act on the target tissue, but as a large force is not required for the activity of detaching the gastroepiploic artery 81A and the like, it may be performed with the treatment endoscope 110 without a problem. Also, since the treatment endoscope 100 can be inserted in a body cavity without using a trocar, depending on the content of the procedure, when the manipulator 1 is combined with the treatment endoscope 110, it is possible to further reduce the invasiveness to the patient by reducing the number of holes made in the body wall.

Figure 24:
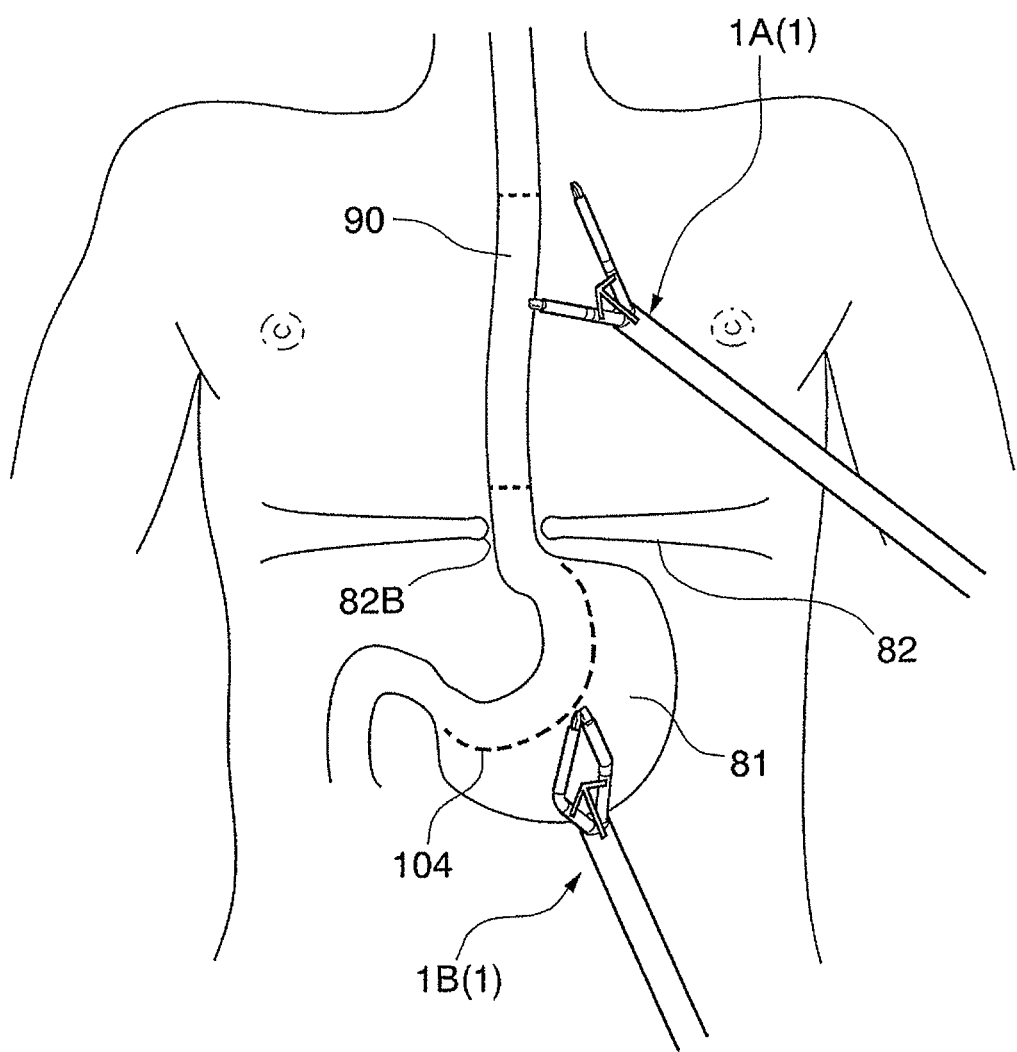
FIG. 24 and FIG. 25 are drawings that show the state of performing a resection of esophagus cancer using the manipulator.
Figure 25:
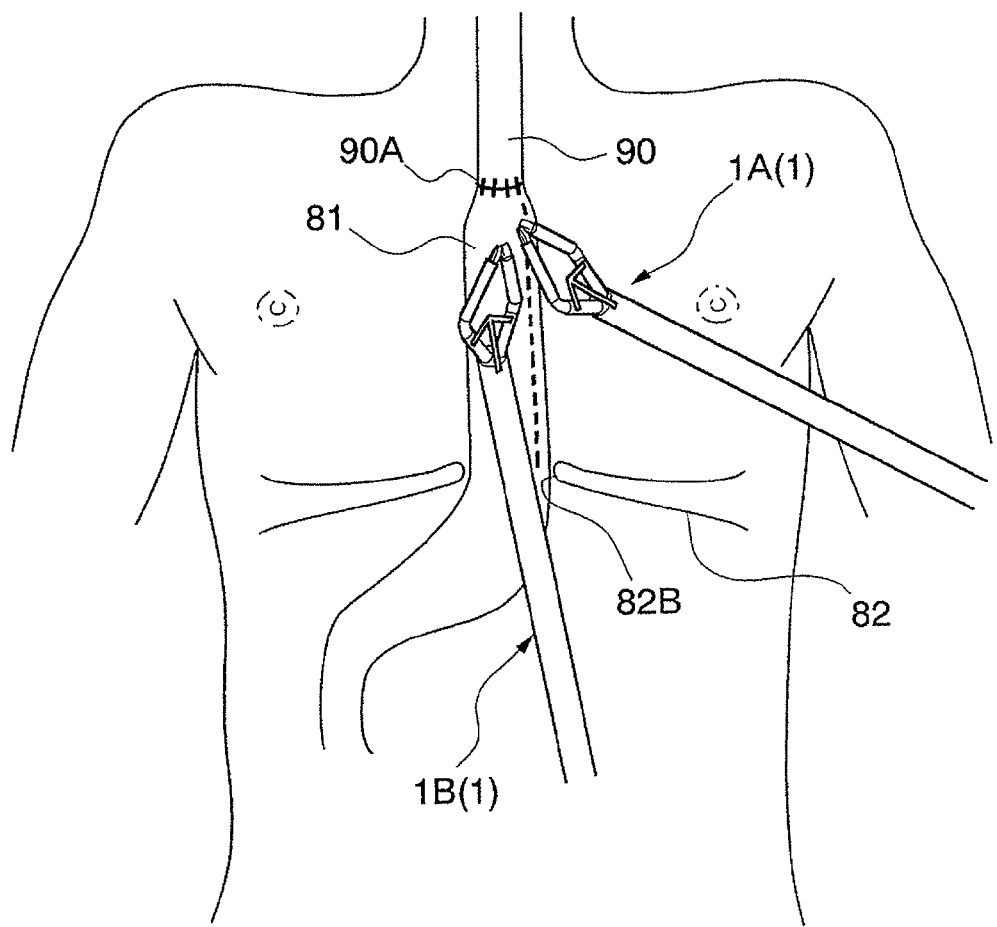

FIG. 24 and FIG. 25 are drawings that show the state of performing a resection of esophagus cancer using the manipulator 1. One operator makes the manipulator 1A advance to the thoracic cavity and performs resection of the esophagus 90 that includes a tumor.

One more operator, in order to perform anastomosis of the digestive tract after resection of the esophagus 90, inserts the manipulator 1B in the abdominal cavity and, as shown in FIG. 24, shapes the stomach 81 in a tubular shape with a stapler 104, and removes the excess portion. When the process of the stomach 81 is finished, the operator on the abdominal cavity side passes the stomach 81 to the operator on the thoracic cavity side via the esophageal hiatus 82B of the diaphragm 82.

The operator on the thoracic cavity side who has received the stomach 81, as shown in FIG. 25, pulls the stomach 81 up to the vicinity of the stump 90A after resection of the esophagus 90 and connects the digestive tract by anastomosis of the stomach 81 and the stump 90A. At this time, the operator on the abdominal cavity side may assist the anastomosis work by advancing the manipulator 1B into the thoracic cavity through the esophageal hiatus 82B or a hole or the like newly formed in the diaphragm as shown in FIG. 25.

Even in the resection procedure of esophagus cancer outlined above, similar to the case of the coronary artery bypass graft, processes of a single operation are performed in two different regions which are separated by the diaphragm 82. However, by using the manipulator 1 of the present embodiment, the procedure time is significantly shortened, and it is possible to reduce the invasiveness. Note that even in the case of performing anastomosis of the digestive tract using an intestine in an esophagus cancer resection operation, it is possible to perform a procedure by following nearly the same steps using the manipulator 1.

Figure 26:
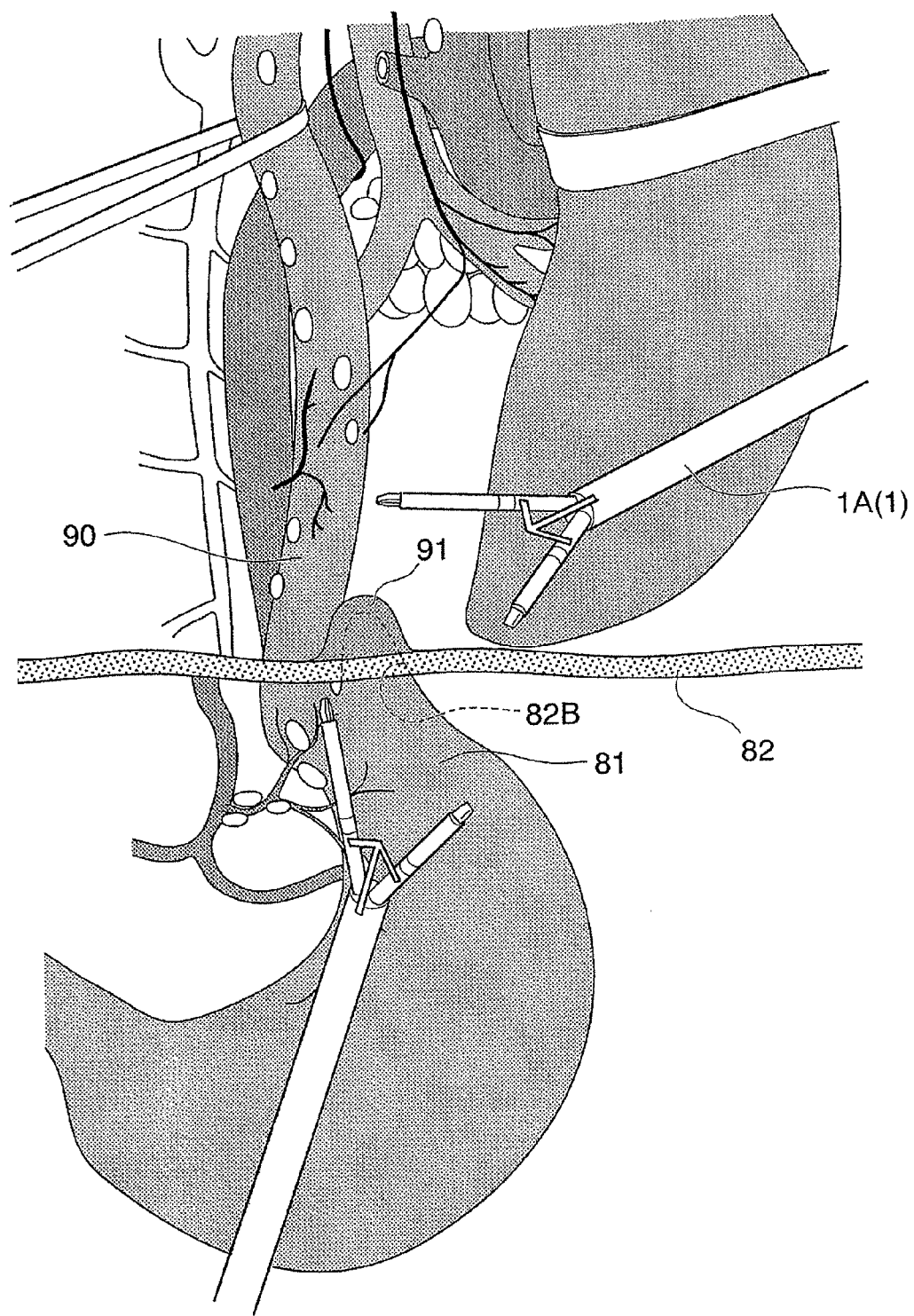
FIG. 26 is a drawing that shows the state of performing treatment of a hiatal hernia using the manipulator.
Figure 27:
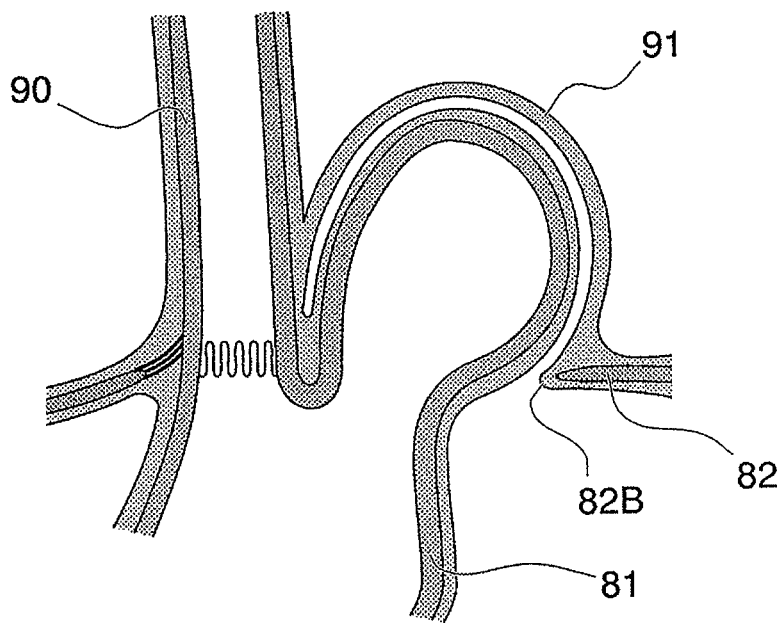
FIG. 27 is a schematic drawing of a hiatal hernia.

FIG. 26 is a drawing that shows the state of performing treatment of a hiatal hernia using the manipulator 1. A hiatal hernia, as shown in FIG. 27, is a condition in which a portion of the stomach 81 bulges upward through the esophageal hiatus 82B to the thoracic cavity side. In particular, in the case of a complete hernia that has a hernia sac 91, since the thoracic cavity side is not sufficiently visible, performing the treatment by approaching only from the abdominal cavity side is difficult.

When the manipulator 1 of the present embodiment is used, one operator, as shown in FIG. 26, inserts the manipulator 1A into the thoracic cavity and accurately performs resection of the hernia sac 91 while performing observation in the thoracic cavity, and another operator working in parallel draws back a portion of the stomach 81 that has bulged upward to the abdominal cavity side. Then the esophageal hiatus 82B is sutured smaller, and the procedure is finished. This suturing may be performed by the two operators collaboratively.

In this way, even in cases of the procedure not being easy such as a complete hernia, by applying the manipulator 1, it is possible to perform it accurately and in a short time.

The aforementioned 3 examples are examples in which two regions are separated by the diaphragm. However, the dividing wall which separates two regions is not limited to the diaphragm. Other examples of the dividing wall are a wall surface of the bladder, a wall surface of the uterus, or the pericardium can be cited.

In the aforementioned three examples, examples in which parts of the operation having the same objective are performed in different regions are described. However, as well as the first pattern, a plurality of independent procedures having different objectives may be performed in each of the regions.

The third pattern is one that performs a procedure on the same target tissue from different directions. By performing procedures from different directions, even the procedures with respect to a plurality of locations which are relatively close with each other such as the same organ or tissue, it can be regarded as performing procedures with respect to different regions in accordance with the present invention.

Figure 28:
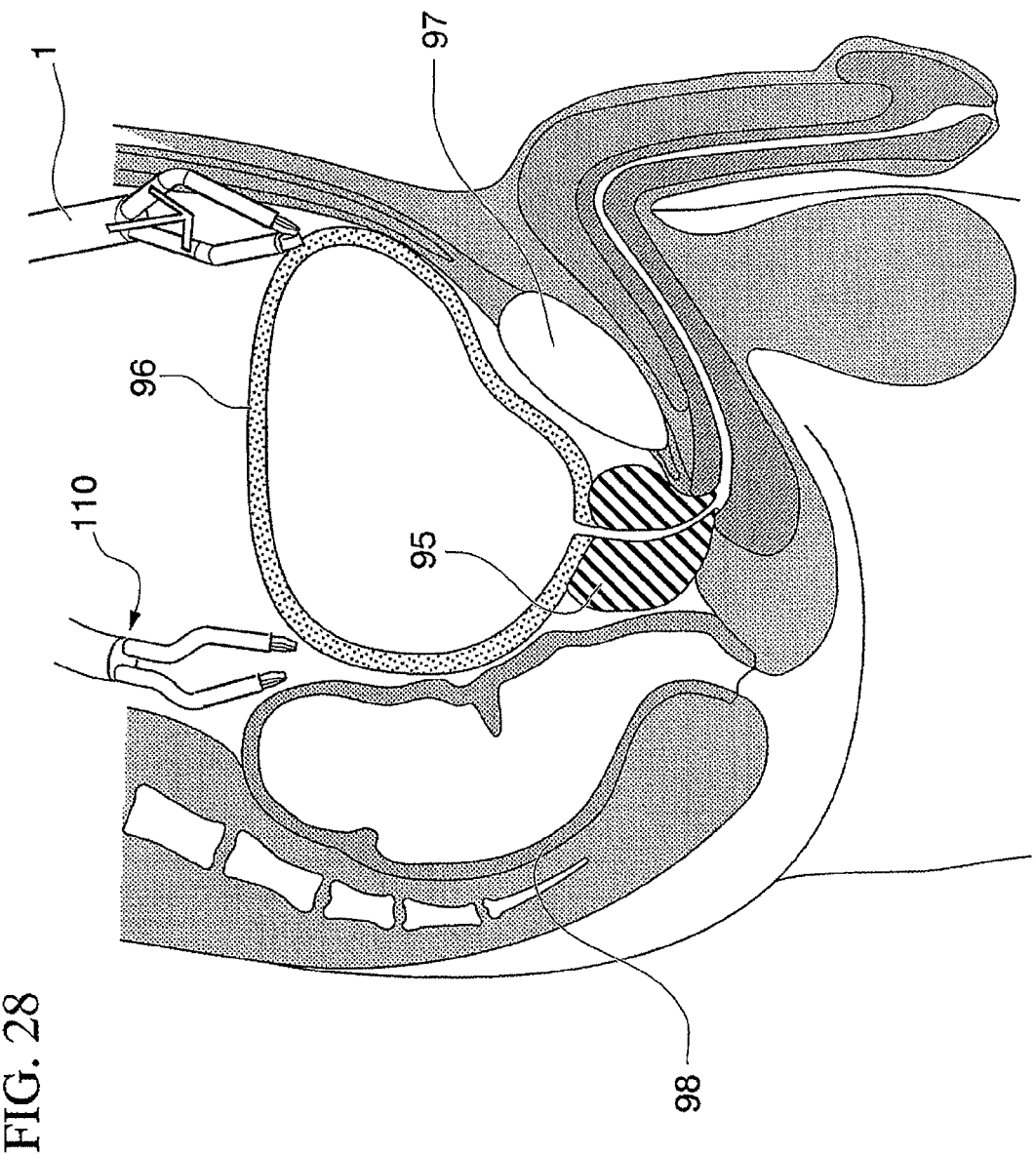
FIGS. 28 to 30 are drawings that show the state of performing a resection of prostate cancer using the manipulator.
Figure 29:
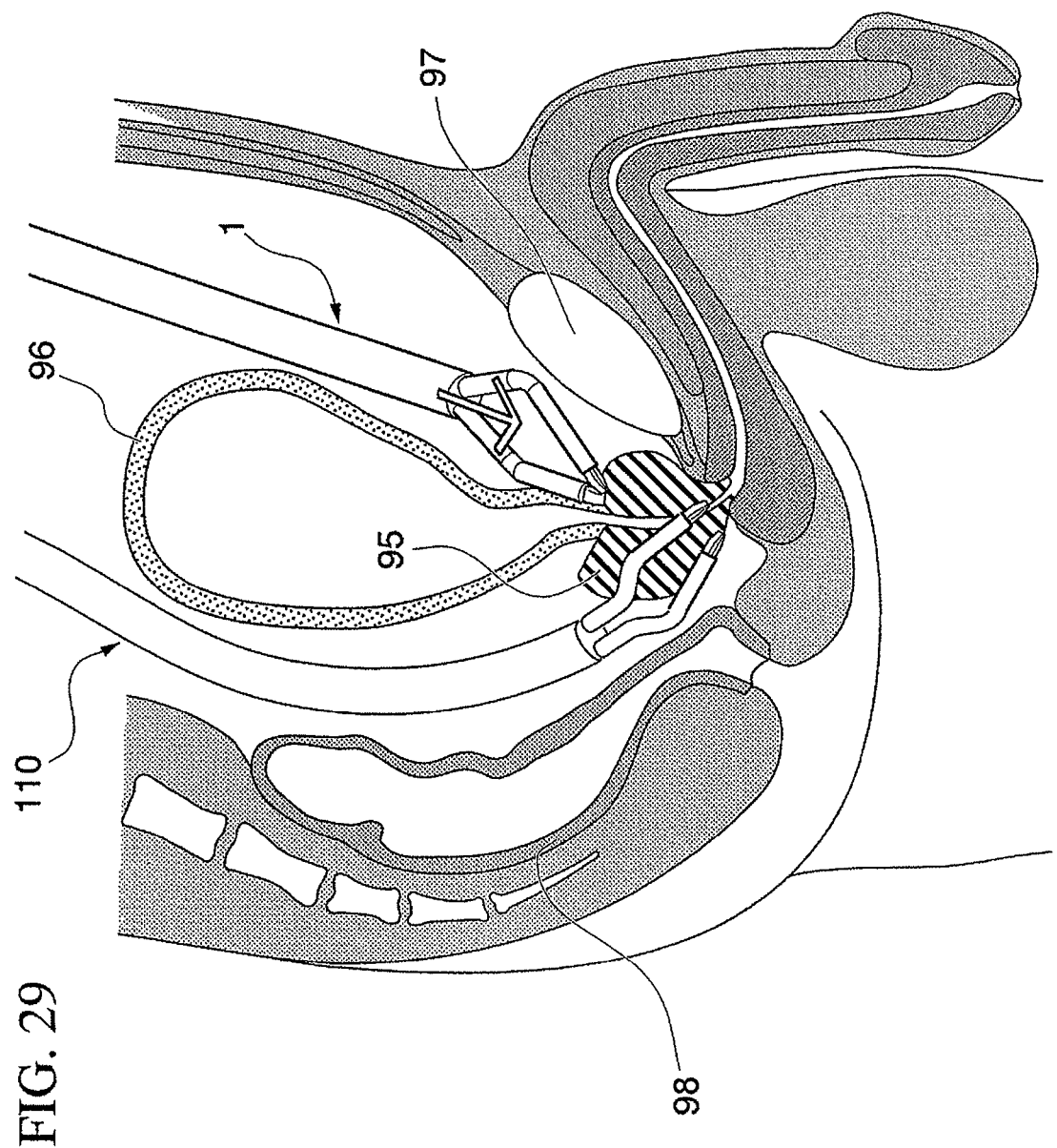
Figure 30:
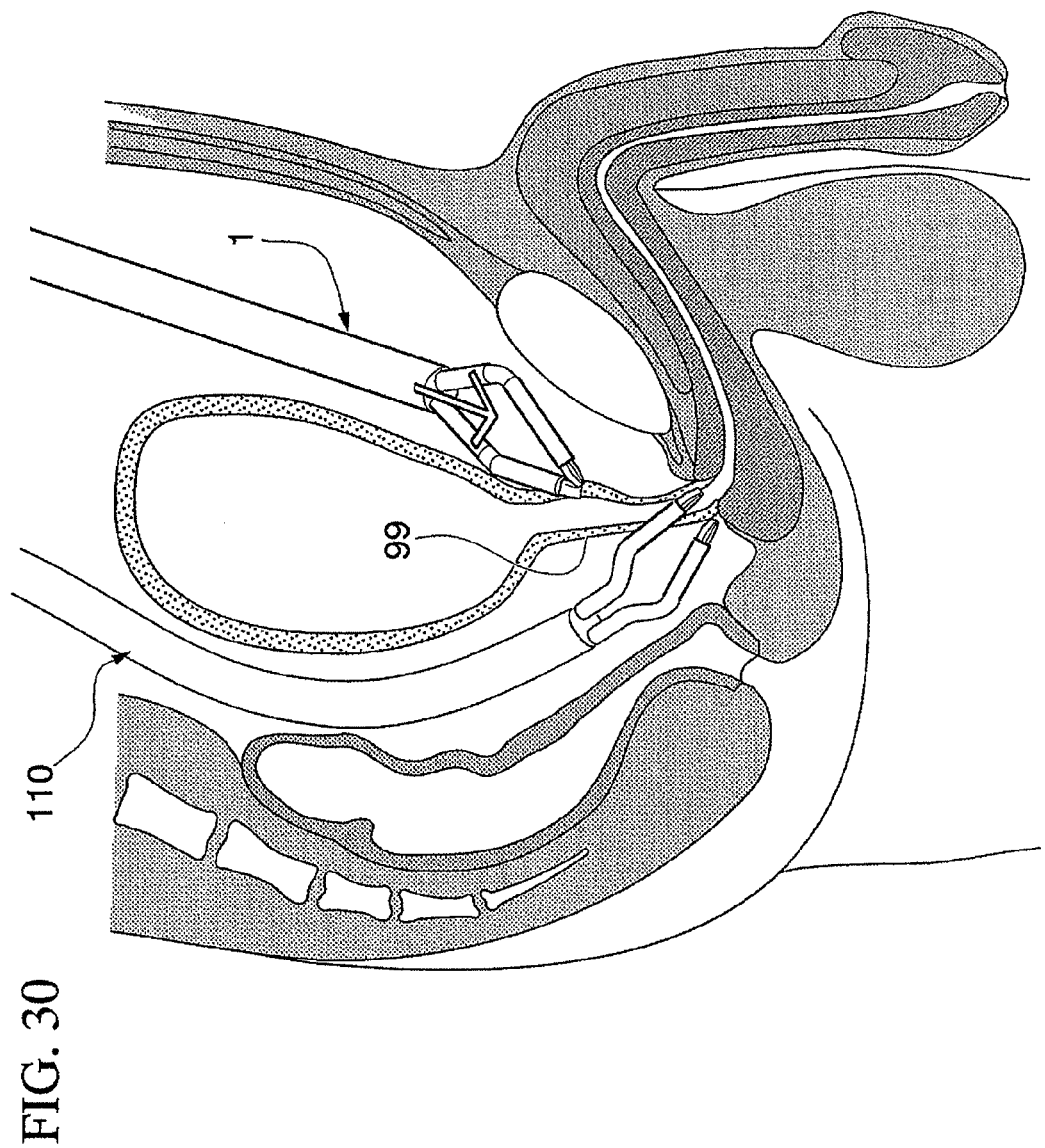

FIGS. 28 to 30 are drawings that show the state of performing a resection of prostate cancer using the manipulator 1. Since the prostate 95 is housed within the pelvis, there is limited space around it. For that reason, it has conventionally been necessary to carry out a procedure by inserting a treatment instrument from the abdominal side, performing a procedure, once removing the treatment instrument and then inserting it again from the dorsal side, and thus when intending to peform procedures without the laparotomy, the procedure has taken a long time.

In the case of using the manipulator 1, as shown in FIG. 28 and FIG. 29, one operator inserts the manipulator 1 from the abdominal side between the bladder 96 and the pubic bone 97 where the entry path is comparatively straight, and the one operator proceeds with the procedure on the prostate 95 from the abdominal side. Another operator inserts a treatment endoscope 110 between the bladder 96 and the large intestine 98 and proceeds with the procedure on the dorsal side of the prostate 95. Since the large intestine 98 is easily wounded, it is preferable to use a treatment endoscope 110 with a flexible insertion portion. In this kind of procedure, since it is substantially impossible to image capture the prostate 95 from the abdominal side and the dorsal side simultaneously with a field of view of the photographic device, in accordance with a definition of the present invention, the abdominal side and the dorsal side of the prostate 95 are different regions even though they are locations of the same organ.

After resection of the prostate 95, the two operators perform suturing of the urethra 99. At this time as well, as shown in FIG. 30, one operator performs suturing of the abdominal side with the manipulator 1, and the other operator performs suturing of the dorsal side with the treatment endoscope 110 or the like, and thus proceed with the suturing in parallel. By carrying out a procedure involving different multiple regions from different angles in this manner, it is possible to significantly shorten the time required for the procedure.

Figure 31:
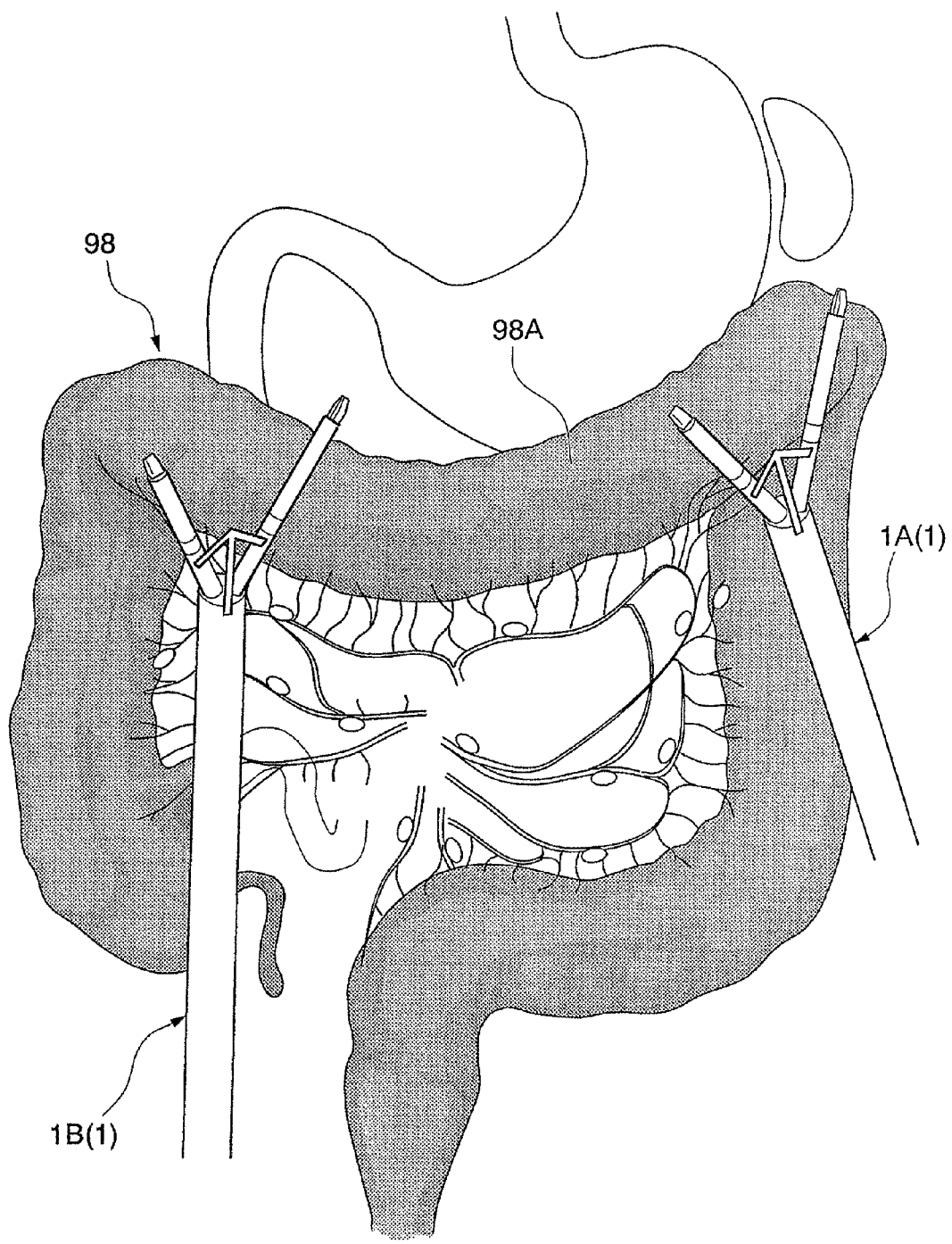
FIGS. 31 to 33 are drawings that show the state of performing a procedure on the large intestine using the manipulator.
Figure 32:
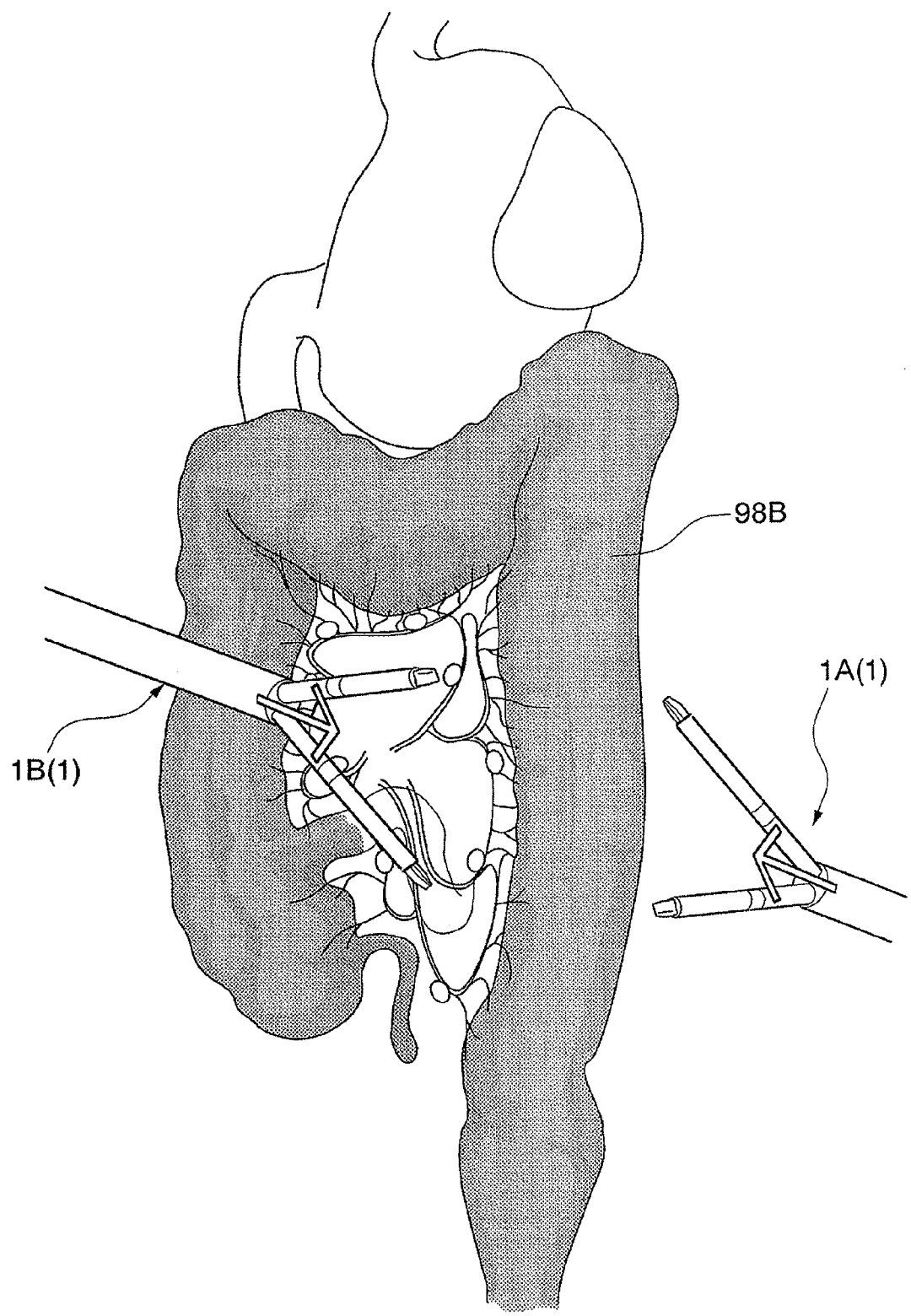
Figure 33:
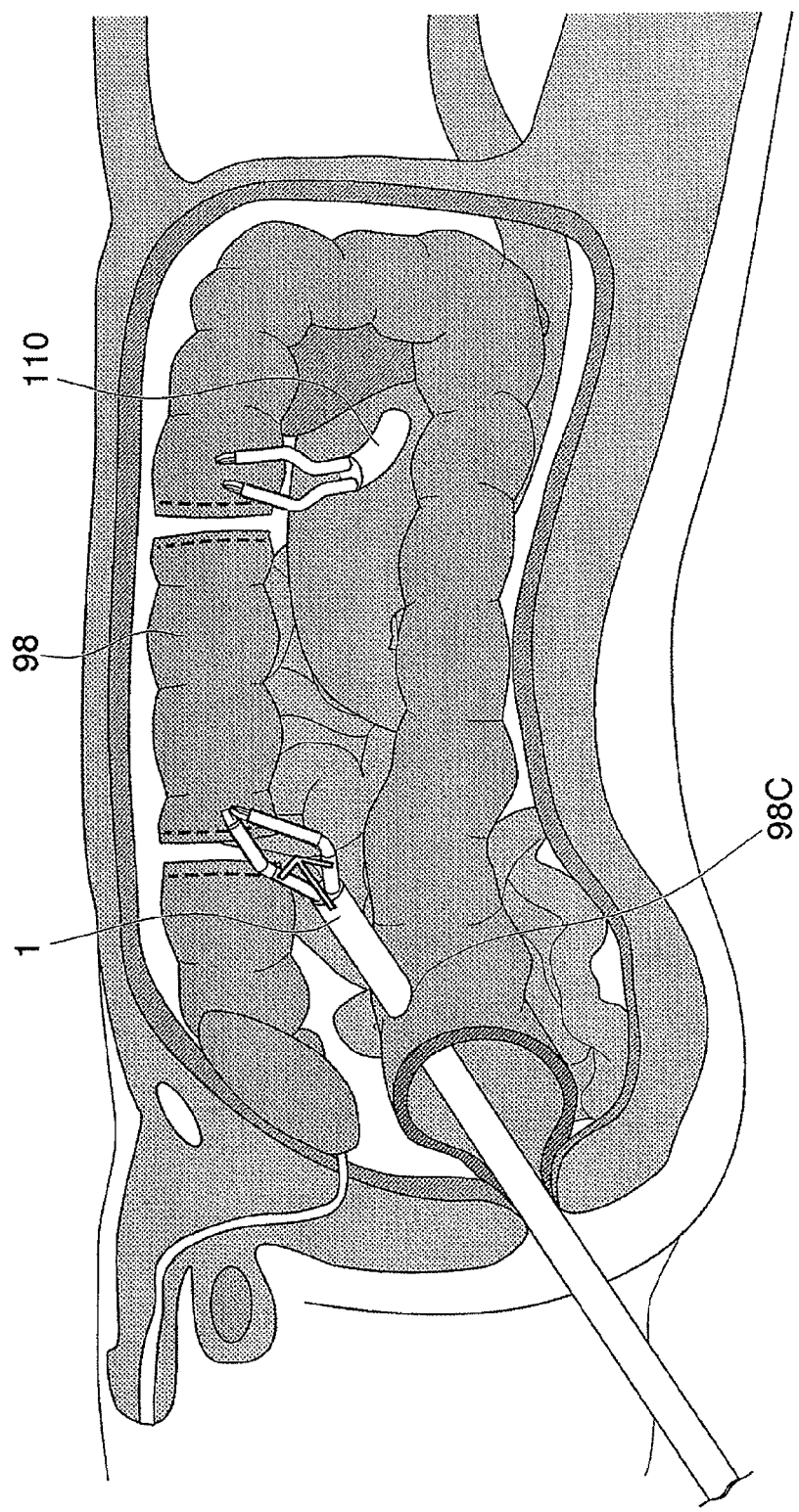

FIG. 31 to FIG. 33 are drawings that show the state of performing a procedure on the large intestine using the manipulator 1. For a large internal organ such as the large intestine 98, many tasks are involved such as detachment prior to resection and blood vessel treatment and the like, and so the procedure takes a lot of time.

Therefore, one operator performs a procedure on the left side region of the transverse colon 98A using the manipulator 1A as shown in FIG. 31, and another operator performs a procedure on the right side region using a manipulator 1B. By thus dividing up the procedure into parts that are carried out simultaneously, it is possible to carry out the procedure in a shorter time. In this case as well, if two regions are located in a positional relationship that it is difficult to simultaneously perform each of the procedures by using one field of view of the photographic device, it is regarded that those two regions are located in different regions.

Note that at this time, instead of one manipulator, the treatment endoscope 110 may be used that is inserted in a body cavity from a suitably selected entry path such as the stomach, anus, vagina, or the like.

In an example shown in FIG. 33, the treatment endoscope 110 is inserted from a mouth and approaches the large intestine 98 via a hole made in the gastric wall and the rigid manipulator 1 is inserted from the anus and approaches the large intestine 98 via a hole made in a wall surface of the rectum 98C. In this manner, in accordance with the approaches, it is possible to make the manipulator 1 of the present invention approach the target tissue via the natural orifice formed in the human body. In this case, it is possible to further reduce the invasiveness to the patient by further reducing the number of the holes to be made to be less than the number of treatment instruments.

Also, as shown in FIG. 32, the work may be divided so that the manipulator 1A performs detachment and the like of the back side (dorsal side) of the descending colon 98B, and the manipulator 1B performs detachment and the like of the front side (abdominal side). At this time, one operator may provide assistance by grasping the descending colon 98B so as to facilitate the work of the other operator.

As well as the aforementioned case of the prostate, it is difficult to image capture using one photographic device so that procedures on the abdominal side and the dorsal side of the descending colon 98B can be performed simultaneously. Accordingly, these two regions can be regarded as different regions as well in accordance with the present invention.

Figure 34:
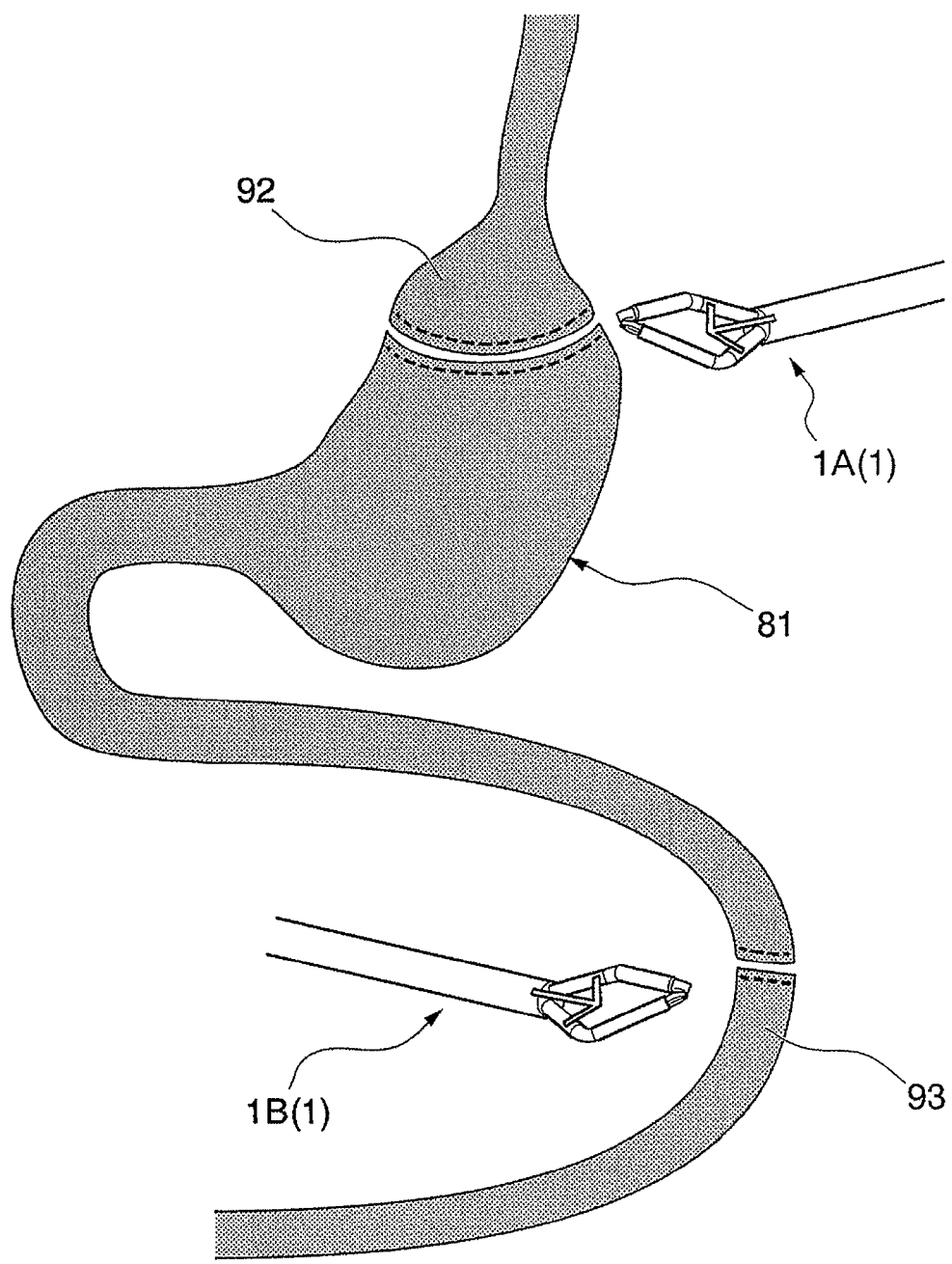
FIG. 34 and FIG. 35 are drawings that show the state of performing the Roux-en-Y method using the manipulator.
Figure 35:
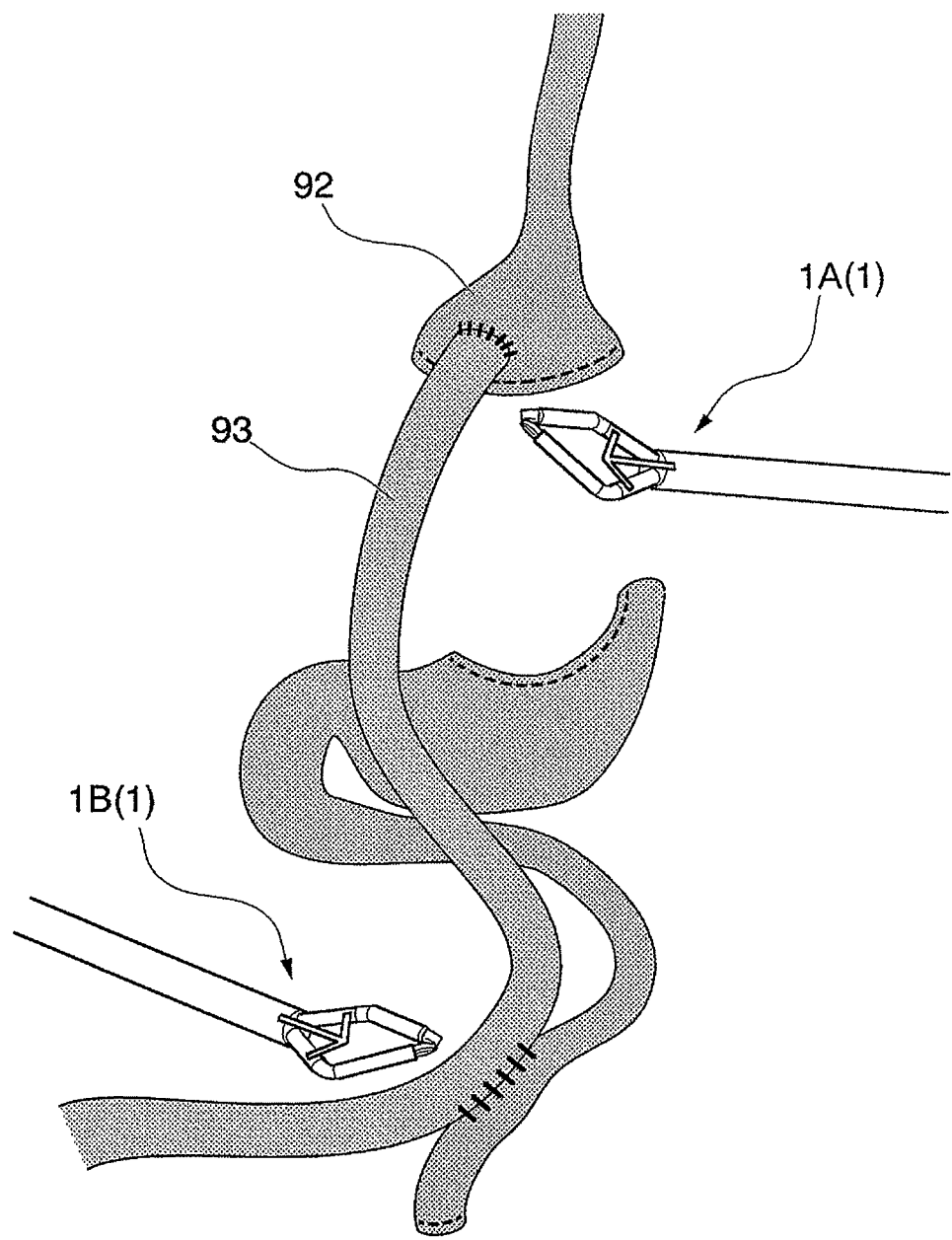

FIG. 34 and FIG. 35 are drawings that show the state of performing the Roux-en-Y method using the manipulator 1. As shown in FIG. 34 and FIG. 35, the processes of formation of the pouch (remaining stomach) 92 and the severing of the small intestine 93 are divided between the manipulators 1A and 1B, respectively, whereby even in the case of procedures performed at separate locations, it is possible to carry them out simultaneously and so complete them in a short time.

While preferred embodiments of the invention have been described and illustrated above, it should be understood that these are exemplary of the invention and are not to be considered as limiting. Additions, omissions, substitutions, and other modifications can be made without departing from the spirit or scope of the present invention.

For example, in the aforementioned explanations, as a case in which two different regions are located in the same body cavity, an example in which both regions are located in the abdominal cavity is used. However, the case is not limited to this example, but other cases in which two different regions are located in the thoracic cavity, that is, in the right chest and left chest for example, may be possible.

The invention is not to be considered as being limited by the foregoing description, and is only limited by the scope of the appended claims.

What is claimed is:

1. A medical manipulator comprising:
    a plurality of arms formed in a cylindrical shape each with a distal end portion of which is made of a rigid member having a bending portion capable of bending,
    an insertion portion made of a rigid member having a plurality of channels in which base ends of the plurality of arms are connected to a distal end of the insertion portion so as to connect lumens of the arms to the plurality of channels,
    a photographic device provided at the distal end of the insertion portion,
    a plurality of operating portions that operates each of the bending portions, and
    a plurality of transmission members that are connected to each of the bending portions,
    a plurality of operating portion links that connect each of the transmission members and each of the operating portions, wherein
    each of the bending portions has:
        a first bending portion that is capable of bending in a predetermined direction by an operation of the operating portion, and
        a second bending portion provided in a base end than the first bending portion that is capable of fixing the plurality of arms in a bent state so as to mutually separate,
    each of the transmission members has:
        a first region which is flexible, and
        a second region which is rigid and connected to a base end portion of the first region,
    each of the operating portions is configured to be capable of being in a straight state along an axial line of the insertion portion and able to be maintained in a state of forming a predetermined angle with respect to the axial line of the insertion portion, and
    with a maximum swing angle of the operating portions during operation being set to be at most the predetermined angle, and
    the second region of the transmission members has:
        a first transmission member for bending the bending portion upward,
        a second transmission member for bending the bending portion downward,
        a third transmission member for bending the bending portion leftward, and
        a fourth transmission member for bending the bending portion downward,
    the operating portion links has:
        a first operating portion link that is connected to a base end of the first transmission member,
        a second operating portion link that is connected to a base end of the second transmission member,
        a third operating portion link that is connected to a base end of the third transmission member,
        a fourth operating portion link that is connected to a base end of the fourth transmission member,
    the distal ends of the first operating portion link and the second operating portion link that serve as turning support points when the operating portion and the insertion portion are made to form the predetermined angle are disposed on a bisectional line of distal end support points of the third operating portion link and the fourth operating portion link when the bending portion is in a linear state.

2. The medical manipulator according to claim 1, wherein the operation portion and the transmission members are connected via a plurality of operating portion links,
    distances between base ends of the plurality of operating portion links are longer than distances between the second regions of a plurality of the transmission members to which the operating portion links are connected, and
    the plurality of transmission members further comprising an adjustment portion capable of absorbing a difference of travel amounts of the transmission members in an axial line direction by being bent.

3. The medical manipulator according to claim 2, wherein the adjustment portion is provided in the first region so that the difference of the travel amount is absorbed by a portion with flexibility being bent.

4. The medical manipulator according to claim 1, wherein at least one of the operating portions is provided with a second bending operating portion connected to the second bending portion via the transmission member, and
    the second bending operating portion is provided with a lock mechanism capable of holding the transmission member so that the second bending portion is fixed in a bent state.

5. A treatment system comprising:
    the medical manipulator according to claim 1;
    a treatment instrument which is capable of being inserted to the channel and the arms of the medical manipulator, wherein
    the treatment instrument comprises:
        a rigid portion that is provided at the distal end of the treatment instrument that performs treatments, and
        a flexible portion that is connected to a base end of the rigid portion,
    when the treatment instrument is inserted to the medical manipulator to a limit, only the rigid portion is projected from the distal ends of the arms and only the flexible portion is located in a lumen of the bending portion.

6. The treatment system according to claim 5, wherein the treatment instrument is configured such that a diameter of the flexible portion is larger than a diameter of the rigid portion, and the arms are configured such that a diameter at least part of each lumen located closer to the distal end than the bending portion are set so that the rigid portion can enter but the flexible portion cannot enter.

7. The medical manipulator according to claim 1, wherein the operating portion is able to swing about an axial swing center, and
    the swing center of the operating portion during the operation is away from the axial line of the insertion portion.

* * * * *